(12) United States Patent
Prediger et al.

(10) Patent No.: US 12,319,906 B2
(45) Date of Patent: Jun. 3, 2025

(54) DETECTING FOAM IN A BIOREACTOR PLANT

(71) Applicant: Sartorius Stedim Biotech GMBH, Göttingen (DE)

(72) Inventors: Andreas Prediger, Göttingen (DE); Sina Götemann, Bovenden (DE); Marco Leupold, Göttingen (DE); Jochen Scholz, Göttingen (DE)

(73) Assignee: Sartorius Stedim Biotech GMBH, Gottingen (DE)

( * ) Notice: Subject to any disclaimer, the term of this patent is extended or adjusted under 35 U.S.C. 154(b) by 100 days.

(21) Appl. No.: 17/800,427

(22) PCT Filed: Oct. 16, 2020

(86) PCT No.: PCT/EP2020/079148
§ 371 (c)(1),
(2) Date: Aug. 17, 2022

(87) PCT Pub. No.: WO2021/170259
PCT Pub. Date: Sep. 2, 2021

(65) Prior Publication Data
US 2023/0125762 A1    Apr. 27, 2023

(30) Foreign Application Priority Data
Feb. 26, 2020  (EP) ..................................... 20159456

(51) Int. Cl.
*C12M 1/21* (2006.01)
*C12M 1/00* (2006.01)
(Continued)

(52) U.S. Cl.
CPC ............ *C12M 41/02* (2013.01); *C12M 23/14* (2013.01); *C12M 23/28* (2013.01); *G01D 5/24* (2013.01); *G01F 23/26* (2013.01); *H03K 17/955* (2013.01)

(58) Field of Classification Search
CPC ...... C12M 41/02; C12M 23/14; C12M 23/28; G01D 5/24
See application file for complete search history.

(56) References Cited

U.S. PATENT DOCUMENTS 3,306,341 A   2/1967 Pugh et al.
3,427,252 A   2/1969 Gaughan et al.
(Continued)

FOREIGN PATENT DOCUMENTS

DE   202011107423 U1   1/2012
DE   102015114510 A1   3/2017

OTHER PUBLICATIONS

International Search Report for International Application No. PCT/EP2020/079148, issued Dec. 10, 2020.

*Primary Examiner* — Dominic E Hawkins
(74) *Attorney, Agent, or Firm* — Quinn IP Law

(57) ABSTRACT

System for detecting at least one presence of foam of a medium in a bioreactor plant, wherein the system comprises: —a bioreactor plant having at least one disposable container for receiving the medium that may comprise the foam; and—at least two capacitive sensor units which are attached at at least two different situating positions of the bioreactor plant, wherein the capacitive sensor units each comprise at least one electrode system for capacitive measurement and are able to detect the presence of foam at the at least two situating positions on the basis of the capacitive measurement; and wherein the capacitive sensor units are designed to transmit captured data relating to the presence of foam to at least one monitoring unit for monitoring, open-loop (Continued)

and/or closed-loop control of foam formation in the bioreactor plant on the basis of said data.

13 Claims, 7 Drawing Sheets

(51) Int. Cl.
*G01D 5/24* (2006.01)
*G01F 23/26* (2022.01)
*H03K 17/955* (2006.01)

(56) References Cited

U.S. PATENT DOCUMENTS

| | | | |
|---|---|---|---|
| 2011/0187388 A1* | 8/2011 | Ossart | C12M 23/28 |
| | | | 324/649 |
| 2017/0184421 A1 | 6/2017 | Sattler et al. | |
| 2018/0223240 A1* | 8/2018 | Damren | C12M 23/14 |
| 2020/0115669 A1* | 4/2020 | Bremer, Jr. | C12M 41/02 |
| 2020/0224144 A1* | 7/2020 | Love | C07K 16/1003 |

* cited by examiner

DETECTING FOAM IN A BIOREACTOR PLANT

TECHNICAL FIELD

The invention relates to a system, a method, and a capacitive sensor unit for detecting the presence of foam in a medium on at least one position in a bioreactor plant and to a method for installing a system for recording a presence of foam in a bioreactor plant.

BACKGROUND

Monitoring bioreactors and bioreactor plants concerning the generation of foam is important for executing a process within a bioreactor because any bursting of foam bubbles causes shear forces that can damage cells and proteins. Such a process can in particular comprise a biochemical process, for example a fermentation process. Likewise, it can happen that a material or a substance present in a foam is substantially not governed by the predetermined process steps. As a result, a foam can potentially be less thoroughly mixed than a fluidic medium, in particular a liquid. Likewise, a temperature can be less accurately controlled within a foam than in a liquid. Additionally, there is the risk that undetected foam for example grows into the exhaust filter of a bioreactor plant and blocks a filter there. This can potentially result in a very rapid pressure increase in the bioreactor plant. Any further addition of gas is then no longer possible, therefore preventing a closed loop control of the oxygen concentration in the liquid medium. It can happen as a result that the entire media filling of the bioreactor plant must be discarded. In a worst-case, this can result in loss of production and high costs. Foam therefore represents a problem in bioprocesses.

The pharmaceutical industry, for example, detects foam as an interference factor using conductivity sensors. However, these have the disadvantage that they need to come into direct contact with the foam to detect the latter.

Depending on process conditions and the organisms in use, foams with different properties can potentially be generated and can in particular exhibit different rates of growth. Foam sensors and anti-foaming agents are therefore regularly in use. Bioreactors are presently already monitored for the presence of foam.

For example, the patent document DE 102010007559 A1 describes a bioreactor vessel having an optical foam sensor comprising a foam contact surface for making contact to the foam to be detected. Bioreactor vessels with optical foam sensors are also known from EP 1 950 281 B1.

However, there continues to be a need to reliably and efficiently detect in particular fast-growing foam within bioreactor plants. According to one aspect, the task is therefore to provide a reliable and efficient system for detecting foam. Analogously, the task according to other aspects also includes providing a capacitive sensor unit for detecting foam and a method for installing a system for detecting foam, with respectively improved reliability and efficiency. In particular, foam growth in bioreactor plants is to be detected with single-use containers because single-use containers are increasingly used in bioreactor plants. In particular, the foam is to be detected without the sensor having to be brought into direct contact with the foam or the cultivation liquid respectively. The measurement should therefore be as noninvasive as possible.

SUMMARY

According to one aspect, a system for detecting at least a foam or the presence of foam of a medium respectively, for example a foam level in a bioreactor plant, comprises the following:
   a bioreactor plant having at least one single-use container, in particular a single-use bag for receiving the medium that can comprise the foam and in particular can generate the foam; and
   at least two capacitive sensor units that are arranged and/or can be arranged at at least two different situating positions or measurement positions respectively of the bioreactor plant,
wherein the capacitive sensor units each comprise at least one electrode system for a capacitive measurement, in particular a permittivity measurement, and can detect the presence of foam at the at least two situating positions on the basis of the capacitive measurement; and; wherein the capacitive sensor units are formed to transfer recorded data concerning the presence of foam to at least one monitoring unit for monitoring, open-loop control and/or closed-loop control of foam formation, wherein the monitoring unit is in particular equipped with a computing unit and/or an open-loop and/or closed-loop control unit for monitoring or recording, each in particular for monitoring, open-loop control and/or closed-loop control of foam formation in a bioreactor plant based on the recorded data.

Preferably, the foam level can be inferred by attaching the capacitive sensor units at specific points, because the foam frequently rises uniformly in the bioreactor. The attachment at several points allows the foam level to be monitored in stages.

The system has the advantage that the foam production can be detected and potentially continuously monitored at several situating positions. As a result, countermeasures to reduce foam can for example be initiated locally at the position where foam is present or were foam is produced respectively. For example, a substance to prevent or at least reduce foam production or an anti-foaming agent respectively can then be introduced at the corresponding location in the bioreactor plant and/or at least one device can be switched off in critical situations and emergencies.

Using a two-point or multi-point controller, foam formation, in particular rapidly expanding foam, can be detected particularly reliably, because firstly, the foam level can be detected within the single-use container, in particular above the medium, and secondly because the presence of foam can be detected within and/or on ports, tubes, and/or hoses. It can for example be the case that the foam above the medium is efficiently counteracted using an anti-foaming agent, whereas the foam inside a tube continues to expand and is not reached by the anti-foaming agent. In this case, corresponding measures to counteract the foam at this position and/or to protect the medium can for example be initiated by switching off at least one device.

The foam level in this case in particular refers to the distance of the foam to the container inner floor. In other words, the foam level in this case in particular is the height of the foam at the highest position from the bottom of the single-use container, wherein the foam can for example sit on a fluidic medium that is filled into the single-use container. In other cases wherein foam bonds on the inner container wall and/or on a port and/or in a hose, this is referred to as the presence of foam. The two-point or multi-point controller is therefore in particular designed to reliably detect the foam level and the presence of foam at at least two positions of the bioreactor unit. The foam level can for example be determined or at least estimated using at least one sensor unit that is in particular arranged on the container wall inner envelope, wherein the presence of foam on a port can be detected using at least a second sensor unit in the vicinity of the port. Alternatively, a sensor unit for determining a foam level can also be arranged or positioned from the outside on the container wall outer envelope.

Such a sensor unit for determining a foam level can in particular also typically be a patch sensor unit that will be described in greater detail below. Such sensor units that are in particular are used to control foam levels in a single-use container of a bioreactor plant can also be referred to as "monitoring patches".

The system can at the same time optionally permit detecting and potentially monitoring the presence of foam in the immediate vicinity of a port. In this case, an arc sensor unit, which will be described in detail below, can for example be preferably arranged from the outside on a port at a corresponding situating position of the bioreactor plant. Such a sensor unit, which not necessarily but preferably represents an arc sensor unit—and which is designed to detect the presence of foam in particular on positions in the vicinity of ports, adapters, hoses, tubes, etc.—can also be referred to as an "alarm patch".

In other words, a further sensor unit, in particular an alarm patch, can be arranged in physical proximity to one or several ports and/or hoses, in particular on and/or for at least one exhaust hose of the bioreactor plant. Such an alarm patch is preferably arranged on the exterior wall of the bioreactor plant, and is in its geometry in particular and substantially differentiated from the geometry of a control patch.

Like all other sensor units, this sensor unit can be read using a transmitter, wherein the transmitter is in contact with a control software of the bioreactor plant, for example using a data cable or a wireless connection. As soon as a signal from the alarm patch exceeds a defined or predetermined threshold, an emergency procedure or an action can be preferably initiated using the controller and/or the monitoring unit of the bioreactor plant. The emergency procedure or action can in particular include switching off the mixer and/or the sparging, along with an optional (rapid) addition of anti-foaming agent.

This described arrangement constellation of the sensor units on the various situating positions is particularly advantageous as this permits monitoring whether a substance that is or must be added to the system to prevent or reduce foam formation or an anti-foaming agent respectively acts efficiently at the various positions within the bioreactor plant.

The antifoaming agent can for example be introduced into the system at a location of the bioreactor plant, but may not develop its full effect at all positions within the bioreactor plant; this in particular affects angles, ports, adapters, tubes and/or hoses. As soon as such a state is detected by an alarm patch, the antifoaming agent can for example be used at a higher level and/or be targeted locally. In emergencies, when for example foam formation cannot be controlled or reduced by merely adding antifoaming agent, an alarm signal can be triggered and/or at least one running device can be switched off.

Alarm patches are preferably also used as an additional safeguard. When the controlled addition of anti-foaming agent based on the data of a control patch does not work as intended and/or malfunctions, for example due to a sensor malfunction, an empty anti-foaming agent reservoir, and/or a pump malfunction, this can be detected at the position of the alarm patch, and corresponding countermeasures can subsequently be introduced by automated or manual means.

In this manner, a 2-point anti-foaming closed loop control can for example be implemented that is designed to automatically perform the following steps: When the presence of foam is detected on a situating position and/or foam is detected that has reached and/or exceeded a predetermined foam level, a pump that adds an antifoaming agent to the interior of the bioreactor plant can as a result be activated for a duration. This can be followed by a waiting time for the effect of the antifoaming agent. When foam is still detected thereafter, the pump can be repeatedly switched on for a duration, repeatedly followed by a waiting time.

In order to avoid inaccurate or erroneous measurements, or to efficiently respond to rapidly growing foam, it is advantageous to arrange a plurality of sensor units on and/or in the bioreactor plant, in particular in the upper half or in the upper third of the bioreactor plant, preferably in the upper quarter.

The advantage of a capacitive sensor unit that is based on the electrode system is that a change of permittivity can be sensed or detected contactlessly or ex-situ, that is to say outside of the single-use container or through the wall of the single-use container. The capacitive sensor unit is substantially based on the capacitor principle. A measurement can also be made in particular through nonconductive layers, such as through foils and/or single-use container sleeves and/or container walls of single-use bags. The electrode system can for example detect based on a change of permittivity whether a foam or a liquid medium, for example an aqueous medium, is present in the immediate vicinity.

When a sensor unit is, or is to be, arranged within the single-use container, the electrode system can be protected against direct contact with the medium using a foil as a shield. In this case, it is also advantageous to form the sensor unit such that it can in particular be sterilized together with the single-use container.

The electrode system can in this case be a two-electrode or in particular a three-electrode system. A two-electrode system has a sensor electrode and a mass electrode, and a three electrode system additionally has a protective electrode. The electrode system is designed to generate or have a capacitance that is determined and influenced by the outer electric field and as a result by the existing permittivity. A change of the capacitance therefore in particular indicates a change of the outer dielectric field and therefore of the existing permittivity of a material, in particular of a medium and/or a foam.

Accordingly, it can then be substantially determined or at least estimated whether or not a medium and/or a foam is present in the immediate vicinity of a situating position. The term "immediate vicinity" in this case indicates a distance within which an electrode system is substantially capable of still detecting a changing permittivity. The distance between the plane within which the electrode system is at least partially arranged and the location of the still just measurable permittivity lies in the near field of the electrodes. Depending on the design of the electoral system, this means for example at values of less than approximately 2 cm, in particular less than approximately 1 cm, and preferably less than approximately 0.5 cm. Signals in particular occur at distances starting at approximately 2 cm, robust measurements are in this case in particular possible starting at approximately 0.5 cm, for example at approximately 0.2 cm or 0.05 cm.

At least one of the sensor units is designed using a transmitter, wherein the transmitter is in contact with the control software and/or the monitoring unit of the bioreactor plant, for example using a cable and/or a wireless connection. As soon as the signal of a sensor unit exceeds a defined threshold, an antifoaming agent can be pumped into the bioreactor, for example by automated means.

Conductive sensor units can be alternatively or additionally used in place of the capacitive sensor units, wherein the sensor units must be in contact with the bioreactor medium. Conductive sensor units can exclusively detect conductive foams.

Preferably, at least one of the capacity sensor units has an adhesive strip with an adhesive surface on which the electrode system can be at least partially arranged, wherein the adhesive strip is in particular designed such that the at least one capacitive sensor unit can be reversibly arranged on the bioreactor plant.

An adhesive strip gives the user the ability to arrange the capacitive sensor unit on a container envelope, preferably from the outside but also from the interior on the bioreactor plant. In particular, a capacitive sensor unit is to be arranged and/or bonded onto a container envelope once. This means that the capacitive sensor unit can in this case only be used at one location of the container envelope, and is disposed after use together with the single-use container or the single-use bag respectively.

Alternatively, the capacitive sensor unit can be arranged multiple times—or more than once—on a surface or wall of the bioreactor plant respectively, for example on the container envelope of the single-use container.

Optionally, the at least one capacitive sensor unit is a capacitive arc sensor unit, wherein the shape of the capacitive arc sensor unit at least sectionally comprises an arc. The arc sensor unit can for example substantially have the shape of a semicircular arc or a three-quarter circle arc, or any other part of a circular arc.

The arc shape can also correspond to an arc having a non-constant radius, for example that of an ellipse arc.

The capacitive arc sensor unit permits a sensor unit to be particularly efficiently arranged on situating positions on which an arrangement is complex. It can then for example be necessary or desirable to detect the foam at a position of a port and/or on a hose and/or on a tube. The capacitive arc sensor unit is designed such that it can be at least partially geometrically positioned around a port or an opening in the single-use container respectively, or can be least partially arranged around the latter. In other words, the capacitive arc sensor unit can at least partially envelop a port, an opening, a projection, a tube, a line, and/or a hose. In this context, "at least partially" means at least approximately 50% of an arc, in particular of a circular arc. This means that the capacitive arc sensor unit for example represents the arc of a semicircle. An arc in this case is a semicircle having a substantially central semicircular recess, therefore providing sufficient space for an opening with a radius r. The radius of the semicircular recess should correspondingly have a radius that at least corresponds to the radius r of the opening.

On bioreactor plants, which have a plurality of openings, ports, hoses and/or tubes, the use of a capacitive arc sensor unit is particularly advantageous because a plurality of sensor units can be arranged on the bioreactor plant in a space-saving manner, in particular without overlapping each other's surface areas.

Alternatively or additionally, this sensor unit can—instead of an arc—also have another shape that mimics or corresponds to a port such that it is at least partially adapted to its outer circumference, or at least partially envelops the latter. In other words, the sensor unit can be adapted to the geometry of a port and/or a hose. The sensor unit can for example also represent a substantially rectangular open or closed frame, that is to say a rectangle with a recess in the center.

Optionally, the bioreactor plant has at least one port, in particular a circular port to form a fluidic connection of the interior of the single-use container to another element and/or to the exterior of the single-use container, wherein a capacitive arc sensor unit can be arranged on the port, and the capacitive arc sensor unit is formed to at least partially envelop, or at least partially form a frame around, the port.

Arranging the capacity arc sensor unit at least partially around a port proves to be advantageous because this arrangement permits determining in a particularly efficient manner whether or not foam is present at a location in the direct or immediate physical vicinity to the port. Even when an antifoaming agent was added in the interior of a container, this can be the case when not all locations, in particular on a port and/or in the interior of tubes and hoses, are reachable by the antifoaming agent, and the foam can then continue to propagate, or can at least not be reduced, in particular in labyrinthine positions within the bioreactor plant.

It is in this case possible to make targeted use of an anti-foaming agent at the position, for example with a nozzle intended for this purpose in the proximity of the foam in order to prevent foam formation at this location. Alternatively or additionally, an alarm and/or an emergency shutoff of the entire system and/or at least an element of the system can be triggered, and/or at least one device, for example a pump and/or a mixing shaft, can be shut off.

Optionally, the bioreactor plant has at least one hose and/or a tube fluidically connected to the port, wherein the at least one capacitive arc sensor unit can be designed to at least partially envelop the hose and/or the tube.

Arranging the capacitive arc sensor unit at least partially around a tube and/or a hose proves to be advantageous because this arrangement permits determining in a particularly efficient manner whether foam is present within the tube and/or the hose.

Even when an antifoaming agent was added in the interior of a container, this can potentially be the case when not all locations, in particular in the interior of tubes and hoses, are reachable by the antifoaming agent, and the foam can then continue to propagate, or can at least not be reduced, in particular in labyrinthine positions within the bioreactor plant.

Optionally, at least one of the capacitive sensor unit, which is preferably a capacitive patch sensor unit, is designed to detect the presence of foam, in particular a foam level or a foam reading, in the single-use container, and one of the capacitive sensor units can preferably be reversibly removable or permanently arranged at a situating position in the interior of the single-use container, in particular on an interior container envelope, wherein the at least one capacitive sensor unit is preferably sterilizable, in particular sterilized.

A substantially rectangular capacitive patch sensor unit can be readily arranged at situating positions that do not require a special geometry of the sensor unit, such as on a planar container envelope.

A system comprised of such sensor units can have two, three, or more sensor units. This is advantageous for detecting the foam level or the fill level within the single-use container. For this purpose, the sensor units can be arranged on the interior container envelope. In this case, it is advantageous to first sterilize the sensor units in order to protect a medium that was filled into the single-use container against contamination. Alternatively, the sensor unit can also be arranged on the exterior container envelope of the single-use container. This has the advantage that a preceding sterilization of the sensor units can be omitted because the container envelope shields the medium against a direct physical contact with the sensor unit. A further advantage is that an end user can decide for themselves how many sensor units are to be arranged on the bioreactor plant and/or at what situating positions the sensor units are to be arranged.

When the sensor units can be arranged reversibly, it is possible to retroactively once again arrange these at other positions or even on different bioreactor plants, for example when a single-use container is disposed.

The foam reading or the foam level is in particular the distance between the container bottom and the highest point of the foam. The foam can in this case for example sit on top of a medium.

Such a sensor unit, in particular a patch sensor unit that is arranged in this manner, can also be called a "monitoring patch" because the latter is intended to monitor a substantially regular or typically expected state of the filling, wherein a critical situation or an emergency situation has not yet been reached.

In this regard, there can also be sensor units, in particular patch sensor units, that are arranged at relatively high situating positions within or outside of the bioreactor plant in order to have the ability to detect a particularly high, not necessarily expected, foam level. For example, such a sensor unit can be arranged directly below a single-use container ceiling or container inner ceiling in order to detect when a foam has reached the ceiling of the container. Such a situation, wherein the foam reaches or exceeds a high level, for example a predetermined level, can potentially be classified as an emergency situation, and it can be desirable that one or several actions are initiated in such a case.

Optionally, at least one of the capacitive sensor units, in particular a capacitive arc sensor unit can be reversibly removably or permanently arranged at a situating position outside of the single-use container, in particular on an exterior container envelope and/or on a port and/or on a hose or tube, or such a capacitive arc sensor unit is already arranged on these.

The capacitive arc sensor unit can in particular act or be used as an "alarm patch", because it is designed to detect the presence of foam in labyrinthine, and in particular at high, positions within the bioreactor plant. There can potentially be an interest in preventing foam formation at such positions, for example within a tube and/or on a port. It can also be the case that an anti-foaming agent was already added to the single-use container, but the effect cannot develop to the same extent within a tube. It is for this purpose conducive to also arrange sensor units on ports and/or tubes and/or hoses.

Such a situation, wherein foam is present on a port, can potentially be classified as an emergency, and it can be desirable that actions are initiated in such a case. A sensor unit that is designed to detect such an emergency can also be called an "alarm patch".

Arranging capacitive arc sensor units has the advantage that foam formation can be detected at labyrinthine positions in a particularly space-saving and efficient manner.

The system preferably comprises the monitoring unit. The monitoring unit can for example comprise a computing unit that receives, processes, and/or forwards the recorded data concerning the foam level or the presence of foam from at least one sensor unit. The monitoring unit can for example also comprise an open-loop and closed-loop control unit that can for example receive data from the computing unit. The open-loop and closed-loop control unit can in particular trigger an action when a predetermined state, for example an emergency state, was detected. The open-loop and closed-loop control unit can preferably trigger an addition of an anti-foaming agent, which is designed to reduce or prevent foam or the production of foam.

Optionally, the monitoring unit is designed to trigger an alarm when the presence of foam is detected at a situating position in the interior of the single-use container using a capacitive sensor unit, in particular by means of a capacitive patch sensor unit, and/or when the presence of foam is detected at a situating position outside of the single-use container using a capacitive sensor unit, in particular by means of a capacitive arc sensor unit.

Optionally, the monitoring unit is designed to trigger an emergency shutoff or to shut off at least one device when the presence of foam is detected using a capacitive sensor unit, in particular by means of a capacitive arc sensor unit on a situating position outside of the single-use container, in particular adjacent to or in the immediate vicinity of a port and/or a hose and/or a tube.

Optionally, the monitoring unit is designed to add a substance to the interior space of the single-use container for the purpose of open-loop control and/or closed-loop control of foam formation, said substance intended to prevent or at least reduce foam formation when a predetermined foam level is detected by at least one capacitive sensor unit on a situating position in the interior of the single-use container and/or on a situating position outside of the single-use container.

Optionally, at least one of the situating positions in the interior of the single-use container and/or outside of the single-use container has a pre-labeled situating position that is suited to indicate the respective situating position for the user and to simplify arranging the respective capacitive sensor unit.

Optionally, the capacitive sensor unit transmits data concerning the presence of foam to the monitoring unit, in particular to a computing unit of the monitoring unit, in each case using a data cable or using a data cable system.

Optionally, the bioreactor plant additionally has an exhaust port to fluidically connect the container interior to the exterior and/or a further component and in particular for evacuating air from the bioreactor plant, in particular from the single-use container. Optionally, the bioreactor plant also has an exhaust hose, wherein the exhaust hose is fluidically connected to the exhaust port.

Optionally, the bioreactor plant also has a filter, in particular a sterile filter that is arranged on the exhaust hose, and that can filter a medium, in particular evacuating air when the latter potentially exits through the exhaust hose. Optionally, the bioreactor plant also has a port for an upper inlet and/or an upper outlet, and preferably a hose and/or a tube fluidically connected thereto.

Preferably, the situating position on the exterior container envelope represents at least one of the following situating positions:
   a situating position at a height slightly below the height of an exhaust port of the single-use container, in particular not in the immediate vicinity of the exhaust port;
   a situating position in the immediate vicinity of the exhaust port;
   a situating position in the immediate vicinity of a port for an upper inlet/upper outlet of the single-use container;
   a situating position on an exhaust hose of the bioreactor plant, wherein the exhaust hose is fluidically connected to the exhaust port and the situating position is located in the immediate vicinity of the exhaust port;

a situating position on the exhaust hose of the bioreactor plant in the immediate vicinity of a filter of the exhaust hose, in particular between the exhaust port and the filter.

In all cases, the term "slightly above" in particular refers to a distance between the respectively stated height and the lower edge of the sensor unit, said distance being between approximately 0.2 cm and approximately 10 cm, in particular between 0.5 cm and 5 cm, and preferably between approximately 1 cm and 3 cm.

In all cases, the term "in the immediate vicinity" or "in the immediate surroundings" or "in the immediate environment" in particular refers to a distance between an edge of an element and an edge of the sensor unit, in particular two edges with the shortest distance to each other, said distance being between approximately 0.2 cm and approximately 10 cm, in particular between 0.5 cm and 5 cm, and preferably between approximately 1 cm and 3 cm.

The situating positions of the sensor units in the proximity of, or approximately at, the height of, or slightly below, an exhaust hose can advantageously serve to detect a state wherein a foam, in particular a rapidly propagating foam, propagates into, or enters, the exhaust hose and potentially blocks the latter, therefore preventing exhaust air from reliably exiting or contaminating filters on the exhaust hose with the foam. Such a case can represent an emergency; as a result immediate actions can be initiated, for example by automated and/or manual means, to prevent a further propagation of the foam. For example, a mixing shaft can be switched off and/or a part of the medium can be evacuated and/or an anti-foaming agent can be added and/or a port, for example the exhaust port, can be closed using a valve.

Optionally, the situating position on the interior container envelope represents at least one of the following situating positions:

a situating position in the proximity of, preferably at a height slightly above a height of a predetermined maximum fill level of the single-use container, in particular above a limit line of a predetermined maximum fill level;

a situating position in the proximity of, preferably at a height slightly above a height of a predetermined minimum fill level of the single-use container, in particular a limit line of a predetermined minimum fill level;

a situating position at a height between the height of the predetermined minimum fill level and the height of the predetermined maximum fill level, in particular between a limit line of the predetermined minimum fill level and a limit line of the predetermined maximum fill level.

The range information stated above must in particular also be used in this case when interpreting the terms "in the immediate proximity of" and "slightly above".

Depending on the size of the bioreactor plant and/or the container, the distance between a sensor unit and the corresponding predetermined fill level is preferably at least between approximately 2 cm and approximately 9 cm. In other words, a sensor unit is preferably arranged between approximately 2 cm and approximately 9 cm above the predetermined minimum and/or maximum fill level.

The described situating positions of the sensor units are in particular advantageous for recording foam levels that can typically be anticipated or can occur in normal operations of the bioreactor plant. Although the sensor units can in the described situating positions also detect emergency situations, in particular the sensor unit that can be arranged slightly above a predetermined maximum fill level, the sensor units are in particular designed to detect foam levels that do not yet generate an emergency situation.

A combination of such sensor units that are arranged to detect typical foam levels and such sensor units that are arranged to detect emergency situations can be particularly advantageous, firstly because the situation within the single-use container can be monitored, and secondly because the presence of foam can be detected on a port and/or in a tube and/or a hose. Based on this approach, a most comprehensive situational status can be detected when for example adding an anti-foaming agent already causes the foam to substantially recede within the container, but the effect of the anti-foaming agent cannot yet develop within the tube, and the foam is still present or even continues to expand within the tube. For example, anti-foaming agent can then be repeatedly added, in particular at a specific position at which foam is detected. Moreover, the system can be controlled using at least two sensor units. A plurality of patch sensor units is preferably used. In particular, for example five, six, seven, eight, nine, or 10 patch sensor units can then be arranged on the bioreactor plant. Alternatively, more or fewer patch sensor units can also be arranged on the bioreactor plant.

The patch sensor unit can in this case be a monitoring patch, and the arc sensor unit can be an alarm patch. In particular, an alarm patch can trigger an action on a port, such as an interlock emergency shutoff for at least one device, in particular when the controller for an anti-foaming addition malfunctions.

Optionally, the system has the following situating positions at which respectively at least one sensor is, or can be, arranged:

a situating position, in particular for a monitoring patch, in the proximity of, preferably at a height slightly above a height of a predetermined maximum fill level of the single-use container, in particular above a limit line of a predetermined maximum fill level;

a situating position, in particular for an alarm patch, in the immediate vicinity of the exhaust port.

In this system, the signal from the monitoring patch can in particular act as a closed-loop control for the anti-foam addition. In a normal case, the alarm patch does not trigger an action when sufficient anti-foaming agent is added to prevent pronounced and/or rapid foam formation. The alarm patch in particular acts as a "secondary safeguard" to intervene before the exhaust filter is blocked in case the anti-foaming agent addition malfunctions, for example if triggered by a malfunctioning control patch or when the anti-foaming agent is insufficiently effective. Triggering the alarm patch in particular serves to shut off foam-promoting actuators in bioreactors, such as a sparging unit and/or a mixing unit. Combining any control patch with any alarm patch is advantageous for this purpose.

Optionally, the system has the following situating positions at which respectively at least one capacitive sensor unit is, or can be, arranged:

a situating position, in particular for a monitoring patch, in the proximity of, preferably at a height slightly above a height of a predetermined maximum fill level of the single-use container, in particular above a limit line of a predetermined maximum fill level;

a situating position, in particular for a first alarm patch, in the immediate vicinity of the exhaust port;

a situating position, in particular for a second alarm patch on the exhaust hose of the bioreactor plant in the immediate vicinity of a filter of the exhaust hose, in particular between the exhaust port and the filter.

In the event that the monitoring patch and also the first alarm patch both malfunction, an alarm can still be triggered and/or foam-promoting actuators in the bioreactor can be switched off by a signal from the second alarm patch.

Optionally, the system has the following situating positions on the container envelope, for example on the interior container envelope, on which respectively at least one capacitive sensor unit, in particular at least one capacitive patch sensor unit, is or can be arranged:

a situating position, in particular for a first monitoring patch, in the proximity of, preferably at a height slightly above a height of a predetermined maximum fill level of the single-use container, in particular above a limit line of a predetermined maximum fill level;

a situating position, in particular for a second monitoring patch, in the proximity of, preferably at a height slightly above a height of a predetermined minimum fill level of the single-use container, in particular a limit line of a predetermined minimum fill level;

a situating position, in particular for a third monitoring patch, at a height between the height of the predetermined minimum fill level and the height of the predetermined maximum fill level, in particular between a limit line of the predetermined minimum fill level and a limit line of the predetermined maximum fill level.

The described system can in particular act as an open-loop or closed-loop control for the addition of anti-foaming agent in various phases of the bioprocess. This is for example advantageous when the bioprocess is started with a relatively low fill volume that is in particular increased as cultivation progresses by adding a nutrient. As soon as the media fill level reaches the height of a sensor unit, the latter can be switched off in the automation software, in particular to prevent a substantially continuous addition of anti-foaming agent. Under certain circumstances, for example for a specific setting, in particular a setting for a comparatively low sensitivity of the sensor unit, the latter can principally also be substantially used to detect the media fill level. Preferably, one or several additional of the described capacitive patch sensor units can also be used.

Preferably, one of the capacitive sensor units—irrespective of its shape—is designed to be switched off or disabled. In particular, a capacitive sensor unit that is arranged at a situating position in the bottom third of the bioreactor plant is designed to be switched off.

In particular, the system is designed to switch off one of the capacitive sensor units. In particular, the system is designed to switch off a capacitive sensor unit that is arranged at a situating position in the bottom third of the bioreactor plant.

The ability to switch off a capacitive sensor unit is in particular advantageous when the bioreactor plant is filled with a medium such that the fill level is at a higher level than the situating position of the capacitive sensor unit. The capacitive sensor unit is in this case unable to detect foam, but only able to detect the presence of the medium, which can result in an undesirable result when analyzing the data. Moreover, it is at any rate potentially not required to leave the capacitive sensor unit in an actively measuring state, because the latter is unable to detect foam in this state.

Based on a further aspect, a capacitive arc sensor unit is designed to detect the presence of foam of a medium, in particular in a bioreactor plant, wherein the capacitive arc sensor unit at least partially has a shape that at least sectionally corresponds to an arc, in particular a circular arc, and is designed to at least partially envelop a port and/or a hose and/or a tube.

The measurement surface of the capacitive arc sensor unit, which is in particular used as an alarm patch, substantially has a geometrical design such that it can be, or already is, arranged as close as possible to the adapters of the exhaust hoses, for example at least partially around a port. The capacitive arc sensor unit can in this case envelop the outer circumference of the adapters, for example a round port to a major extent, in particular by more than 50%, for example approximately 50 to 100%, in particular approximately 55 to 90%, and preferably approximately 60 to 70%.

The capacitive arc sensor unit is in this case preferably attached to the bioreactor plant from the outside such that the direction of measurement of the capacitive sensor unit points in the direction of the interior of the bioreactor plant, for example in the direction of the interior of the single-use container or in the direction of the interior of a hose or a tube, in order to detect or record the presence or absence of potentially forming foam. The geometry of the capacitive arc sensor unit has the principal advantage of improved and faster foam detection, that is to say also at situating positions that are unfavorably located for sensor units having other geometries. In particular with respect to the strictly delimiting surface area of the container envelope or the film of a single-use bag or the bioreactor wall and the plurality of elements, such as a mixing shaft, ports, adapters, and hoses on single-use systems or single-use containers of bioreactors, the geometry of the capacitive arc sensor unit proves to be particularly advantageous, space-saving, and efficient. This is in particular the case when the container volume is less than 100 L, for example about 70 L, because the surface of the bioreactor plant in this case offers particularly little space to arrange a plurality of elements.

Likewise, it can be advantageous to arrange a large number of sensor units on a smaller bioreactor plant because a foam can in this case potentially reach critical areas faster due to the small volume.

Preferably, the capacitive arc sensor unit comprises at least one electrode system having a sensor electrode and a protective electrode, and in particular having a mass electrode for capacitive measurements at one of the situating positions on the interior container envelope and/or on the exterior container envelope of the bioreactor plant and for detecting the presence of foam at a situating position on the basis of the capacitive measurement.

The advantage of a capacitive arc sensor unit based on the electrode system is that a change of permittivity can be identified or detected. This can also be accomplished in particular through nonconductive layers, such as through foils and/or single-use container envelopes and/or container walls of single-use bags. The electrode system can for example detect based on a change of permittivity whether a foam or a liquid medium, for example an aqueous medium, is present in the immediate vicinity.

The electrode system can be a two-electrode or in particular a three-electrode system. A two-electrode system in particular comprises a sensor electrode and a protective electrode, and a three-electrode system additionally has a mass electrode. The mass electrode is designed to protect and correspondingly ground the electrode system, and therefore the capacitive sensor unit, against high charges versus mass or ground. The sensor electrode and the protective electrode are designed to generate a capacitance that is determined by the outer dielectric field and as a result by the existing permittivity. A change of the capacitance therefore may indicate a change of the outer dielectric field and therefore of the existing permittivity of a material, in particular of a medium and a foam. Accordingly, it can then be substantially determined whether or not a medium and/or a foam is present in the immediate vicinity of a situating position. The term "immediate vicinity" in this case in particular indicates a distance within which an electrode system is capable of still detecting a changing permittivity. Depending on the configuration of the electrode system, the distance between the plane or the surface area within which the electrode system is substantially arranged or present and the just still measurable permittivity can be at values of less than approximately 1 cm, in particular less than approximately 0.3 cm.

Preferably, at least one section of at least one of the electrodes of the electrode system mimics or at least partially emulates the shape of the capacitive arc sensor unit, wherein the capacitive arc sensor unit preferably has an adhesive strip and the electrodes are optionally at least partially arranged in different layers or planes on the adhesive strip.

An arrangement of the electrode system wherein the at least one section of at least one of the electrodes emulates the shape of the capacitive arc sensor unit is particularly space-saving and in particular permits a particularly efficient measurement or detection or recording of foam. A layered arrangement of the electrode system can advantageously also or additionally be particularly space-saving.

The aforementioned embodiments and features of the system are also used in a corresponding manner by the following methods according to any of the aspects or according to any of the embodiments. The resulting advantages, which were in particular already mentioned, are likewise valid for the method according to the aspect, and in particular according to any of the possible embodiments.

The capacitive arc sensor unit preferably has the following features:
  a field, in particular and arc section for attachment at one of the situating positions;
  a connecting lip for connecting, in particular for electrically connecting, a mains connection and/or a data connection to the electrode system; and
  a spacer designed to at least partially envelop the connecting lip. The spacer should be made of a material with a dielectric constant of less than $\varepsilon_r$ and should be designed to keep foreign bodies at a sufficient distance, such that it cannot relevantly penetrate the field generated by the connecting lip.

A sensor unit, in particular an arc sensor unit or a patch sensor unit, preferably has a spacer that is able to prevent or to even avoid interference signals. The spacer can in particular have a thickness of approximately 0.2 mm to approximately 3 mm, preferably of approximately 0.8 mm to approximately 1.3 mm, and particularly preferably of approximately 1 mm. A thickness of approximately 1 mm permits a high flexibility of the connecting lip 28, while at same time ensuring sufficient spacing from potential foreign bodies to prevent signal coupling into the sensitive ranges of the connecting lip.

The connecting lip is preferably a substantially elongated and in particular flexible connecting lip that can be moved and/or bent such that a connecting unit, in particular such as a mains connection or a power supply and/or a data connection, can be arranged on, or connected to, the sensor unit from various directions using the connecting lip. This gives the user particularly easy access when connecting the sensor unit because the elongated flexible connecting lip can be contacted from several sides by bending the latter toward the user.

The spacer preferably has a shielding plastic, in particular polypropylene, that preferably and at least partially has a thickness of approximately 1 mm.

A connecting lip with spacer gives the user the ability to connect the capacitive arc sensor unit with particular ease, while also not recording false positive signals that can potentially be generated by foreign bodies with high $\varepsilon_r$ in the proximity of the connecting lip.

The spacer can in particular avoid or prevent that the capacitive sensor unit records changes in the permittivity and/or the capacitance in the immediate environment of the connecting lip, and that such changes are only detected in the immediate environment of the arc section.

Alternatively, a capacitive patch sensor unit can also have the following features:
  a field, in particular a rectangular field or patch for attaching on one of the situating positions;
  a connecting lip for connecting, in particular for electrically connecting, a mains connection and/or a data connection to the electrode system; and
  a spacer designed to at least partially envelop the connecting lip.

According to a further aspect, a method for detecting at least one presence of foam of a medium has the following steps:
  Provide a bioreactor plant having at least one single-use container for receiving the medium that can comprise the foam;
  Arrange at least two capacitive sensor units on at least two situating positions of the bioreactor plant, in particular on an interior container envelope and/or on an exterior container envelop of the bioreactor, wherein the capacitive sensor units each have at least one electrode system for a capacitive measurement;
  Record data concerning the presence of foam on the at least two measurement positions based on the capacitive measurements; and
  Transmit the recorded data concerning the presence of foam to at least one monitoring unit for monitoring, in particular for monitoring, open-loop control and/or closed-loop control of foam formation in the bioreactor plant based on the data using the capacitive sensor units.

The method preferably comprises at least one of the steps: Monitor, control by open or closed loop a foam formation in the bioreactor plant using the monitoring unit based on the transmitted data.

Controlling by open or closed loop preferably comprises feeding a substance that is designed to prevent or at least reduce foam formation when the presence of foam is detected by at least one capacitive sensor unit, preferably when the presence of foam is detected by at least one capacitive sensor unit at a situating position outside of the single-use container, in particular using a capacitive arc sensor unit.

The method optionally has the following steps:
  Trigger an alarm when the presence of foam is detected by at least one capacitive sensor unit at a situating position in the interior of the single-use container and/or at a situating position outside of the single-use container; and/or
  Trigger an emergency shutoff when the presence of foam is detected by at least one sensor at a situating position outside of the single-use container.

According to a further aspect, a method for installing a system for detecting at least one presence of foam of a medium in a bioreactor plant comprises the following:

Provide a bioreactor plant having at least one single-use container for receiving the medium that can comprise the foam;

Provide at least two capacitive sensor units, wherein the capacitive sensor units each have at least one electrode system for a capacitive measurement;

Arrange the at least two capacitive sensor units at respectively one situating position of the bioreactor plant, in particular on an exterior container envelope of the bioreactor plant; and Connect the at least two capacitive sensor units to at least one monitoring unit for monitoring, in particular for monitoring, open-loop control and/or closed-loop control of foam formation in the bioreactor plant based on the capacitive measurements.

Metrology properties can preferably be varied. This can for example relate to a variable sensitivity of the transmitter and/or the sensor units (for example about 5, about 10 and/or about 100 pF). Moreover, a sensor unit can also be arranged at a situating position within the bioreactor plant, for example on a mixing unit, in particular on a mixing shaft, in order to be able to measure deeper in the bioreactor plant. These preferred features are in particular advantageous because different organisms can potentially be used in bioprocesses, and because different foams can be generated depending on the assumed process conditions.

DETAILED DESCRIPTION

Figure 1A:
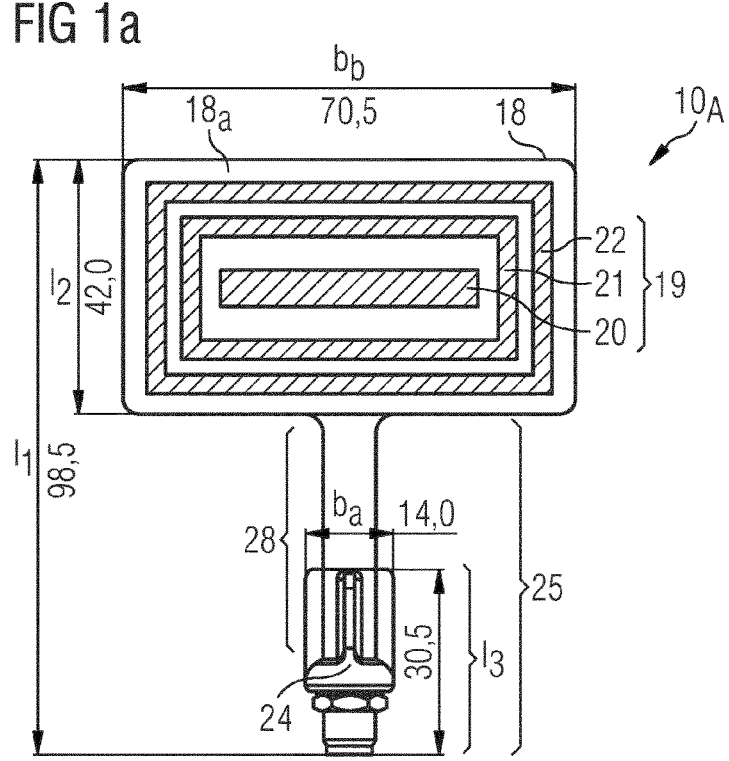
FIG. 1a is a schematic representation of an exemplary patch sensor unit.

The following is a detailed description of several exemplary embodiments, wherein the invention is not limited to the described exemplary embodiments. Several features that are described in a specific embodiment can be arbitrarily combined, provided they do not rule each other out. Moreover, various features that are provided together in the exemplary embodiments are not to be regarded as restricting the invention.

Bioreactors or bioreactor plants are in particular plants having one or several containers to receive media. A bioreactor is generally designed to monitor, control by open and/or closed loop biochemical and/or chemical processes. Bioreactors are in particular used as fermenters for cultivating microorganisms, cells, single-cell and/or multi-cell organisms. A bioreactor can in particular be formed as a single-use container and can comprise further elements of a bioreactor. A bag can for example represent a principal element of a bioreactor, wherein the bag can be held by a stainless steel frame.

The single-use container (or SU container) is in particular design for single use for one or several consecutively running biochemical processes. After use, a single-use container can be disposed without first having to be cleaned using potentially elaborate means.

Media filled into bioreactors and/or intermediate products of these media can under certain circumstances form foam, in particular during mixing operations or during one or during several processes. Foam formation is problematic for several reasons. Firstly, foam can block inlets/outlets and/or ports, and secondly, foam can negatively impact processes within the bioreactor. It is therefore essential to monitor bioreactors and bioreactor plants concerning the generation of foam. It is in particular advantageous to monitor rapidly propagating foams because these can occur in short time frames and because potentially valuable media can be placed at risk in a bioreactor due to malfunctions caused by foam. Fermentation processes are in particular also subject to the risk that not detected foam for example grows or reaches into the exhaust filter of a bioreactor plant and blocks a filter there. This can potentially result in a very fast pressure increase in the bioreactor plant, and can for example prevent a closed loop control of the oxygen concentration of the liquid medium. It can happen as a result that the entire media filling of the bioreactor plant must be discarded. In a worst-case, this can result in loss of production and high costs. It is therefore important to efficiently and continuously detect foam formation.

For this purpose, sensor units, in particular capacitive sensor units, can be arranged on and/or in a bioreactor plant. This involves using at least a two-point monitoring or even a multipoint monitoring, wherein the two-point or multipoint monitoring each require two or more capacitive sensor units at respectively different positions of the bioreactor plant, such that foam formation can be monitored at several positions of the bioreactor plant. A combination of at least one patch sensor unit and at least one arc sensor unit is preferred in this case, wherein the at least one patch sensor unit is in particular arranged to monitor a foam level, and the at least one arc sensor unit is arranged to monitor the presence of foam on a port and/or a hose and/or a tube.

FIG. 1a is a schematic representation of an exemplary capacitive patch sensor unit $10_A$. The capacitive patch sensor unit $10_A$ has a rectangular field $18_a$ with rounded edges. The rectangular field $18_a$ can be at least partially equipped with, or comprise, an adhesive strip 18 for attachment on a container wall. An electrode system 19 is at least partially arranged on or above or in the rectangular field $18_a$. The electrode system 19 is in particular formed as a three-electrode system and has a sensor electrode 20, a protective electrode 21 and a mass electrode 22. Alternatively, the electrode system 19 can in general—that is to say in all embodiments—in particular in the capacitive patch sensor unit $10_A$ also be formed as a two-electrode system instead of as a three-electrode system, and would then only have a sensor electrode 20 and a protective electrode 21. The capacitive patch sensor unit $10_A$ also has a connection section 25 having a connecting unit 24 and a connecting lip 28.

The connecting lip 28 represents a substantially elongated connecting section, in particular an electrically conductive path to supply the electrode system 19 with current or voltage and/or to conduct signals, and on whose one end the rectangular field $18_a$ is located, and on whose other end the connecting unit 24 is located. The connecting unit 24 for example is used for signal transmission and/or power supply. By applying alternating current, an electrical alternating field can be generated in this manner in the electrode system 19, and the resulting current flow can be detected as a signal.

A capacitive sensor unit substantially acts like an open capacitor. In particular, an electrical field is generated between the sensor electrode and the mass electrode. When a material with a dielectric constant $\varepsilon_r$ greater than air penetrates the electrical field, the capacitance of the sensor arrangement increases as a function of $\varepsilon_r$ of this material.

The sensor unit further has an electronic unit that can detect this capacitance increase, and the signal detected in this manner can be analyzed in the subsequent signal processing step.

Sensor units that have a mass electrode, and are therefore based on a three-electrode system, can be installed in, and/or arranged on, a material flush with the active surface—that is to say with the surface from which the electrical field substantially propagates for measurement. Because the electrical field on these sensor units propagates for measurement from the sensor electrode to the integrated mass electrode, a defined electrical field for measurement or a measurement field is generated. Such sensor units are particularly suited for detecting or recording nonconductive materials, such as oils, glass, wood, and/or plastics. But conductive materials can likewise be detected. A further compensation electrode can also be incorporated into the sensor unit, in particular to render the sensor unit resistant to potential dirt deposits and moisture on the sensor surface.

Sensor units that do not have a mass electrode, and are therefore based on a two-electrode system, are generally not installed flush into, and/or arranged flush on, a material. The mass electrode is in this case not integrated into the sensor unit, but is instead formed by the object and/or medium to be detected, in particular by the foam that potentially occurs in the proximity of the sensor unit. Sensor units without a mass electrode are generally relatively resistant to dirt and are particularly suitable for detecting fill levels. Sensor units that do not have a mass electrode are particularly suited for detecting conductive media, in particular media that are grounded.

Capacitive sensor units can in particular detect conductive as well as nonconductive media that have a dielectric constant of $\varepsilon_r > 1$. The dielectric constant $\varepsilon_r$ (also called permittivity constant or dielectric conductivity) of a material determines by how much the electrical flow density increases when the corresponding material penetrates the measurement field instead of vacuum or air.

Conductive materials in particular have an electrical conductivity of >approximately 20 pS/cm. They can generally be relatively reliably detected by all sensor types, including those with mass electrode or those without mass electrode.

Typical media regarded as conductive can for example be the following: Water with ions or salts, blood, ink, milk, acetone, and metallic substances.

Nonconductive media typically have an electrical conductivity of <approximately 20 μS/cm. Such media can be particularly readily detected using sensor units that have a mass electrode, that is to say with three-electrode systems. When a nonconductive object is introduced into the field of the sensor, the field is amplified as a function of the dielectric constant and the size of the material to be detected, and therefore amplifies the capacitance of the sensor arrangement. The lower the value $\varepsilon_r$, the more difficult it is to detect the medium.

The capacitive patch sensor unit $10_A$ can generally have an arbitrary size. An overall length $I_1$ of the capacitive patch sensor unit $10_A$ including the connection section 25 and the connecting unit 24 can in particular be selected such that it ranges between approximately 1 cm and approximately 20 cm, in particular between approximately 3 cm and approximately 15 cm and preferably between approximately 8 cm and approximately 12 cm. In the exemplary case described here, the overall length is approximately 98.5 mm, or approximately 9.85 cm. A length $I_2$ of the rectangular field $18_a$ can in particular be selected such that it ranges between approximately 0.5 cm and approximately 10 cm, in particular between approximately 1 cm and approximately 6 cm and preferably between approximately 3 cm and approximately 5 cm. In the exemplary case described here, the length $I_2$ of the rectangular field $18_a$ is approximately 42 mm, or 4.2 cm.

A width $b_b$ of the rectangular field $18_a$ can in particular be selected such that it ranges between approximately 1 cm and approximately 15 cm, in particular between approximately 3 cm and approximately 12 cm and preferably between approximately 5 cm and approximately 10 cm. In the exemplary case described here, the width $b_b$ of the rectangular field $18_a$ is approximately 70.5 mm, or 7.5 cm.

A width $b_a$ of the connecting lip 28 of the connection section 25 can in particular be selected such that it ranges between approximately 0.2 cm and approximately 5 cm, in particular between approximately 0.5 cm and approximately 3 cm and preferably between approximately 1 cm and approximately 2 cm. In the exemplary case described here, the width $b_a$ of the connecting lip 28 of the connection section 25 is approximately 14 mm, or approximately 1.4 cm.

A length $I_3$ of the connecting unit 24 can in particular be selected such that it ranges between approximately 0.2 cm and approximately 7 cm, in particular between approximately 0.5 cm and approximately 5 cm and preferably between approximately 2 cm and approximately 4 cm. In the exemplary case described here, the length $I_3$ of the connection section 25 is approximately 30.5 mm, or approximately 3.05 cm.

The exemplary capacitive patch sensor unit $10_A$ is designed to be arranged on an interior container envelope and/or an exterior container envelope and/or another element of a bioreactor plant, in particular by means of an adhesive strip 18, such that the electrode system 19 can preferably contactlessly detect a change of permittivity using a capacitive measurement, and determine therefrom whether a foam is present in the immediate vicinity or at an immediate distance or in the immediate surroundings or environment.

The connecting unit 24 can in particular have an M8 connector. The connecting lip 28 of the connection section 25 can in particular be connected to this M8 connector and can have a potting compound that holds both elements together. The potting compound can in particular be comprised on an ABS plastic. The electrode system 19 is connected to the connecting unit 24 in particular by means of a distribution line.

Figure 1B:
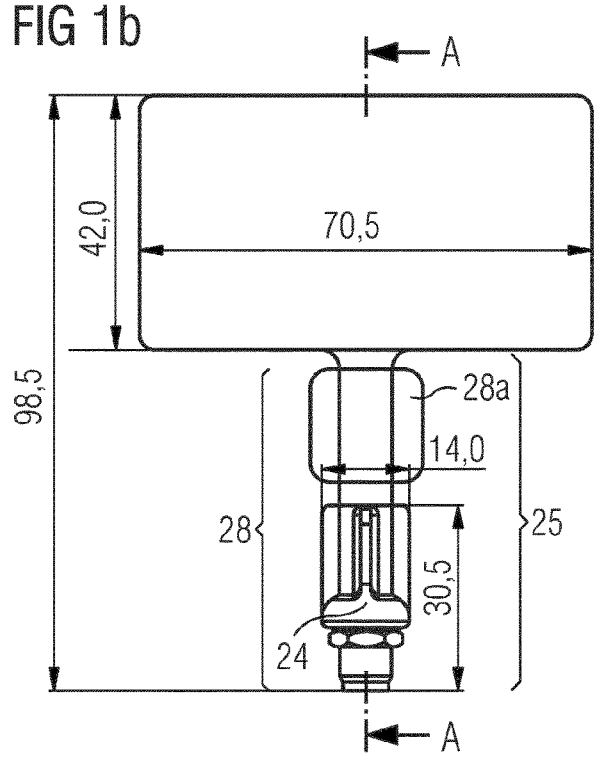
FIG. 1b is a schematic representation of an exemplary patch sensor unit having a spacer on a connecting lip.

FIG. 1b is a schematic representation of an exemplary patch sensor unit $10_A$ having a spacer 28a on the connecting lip 28. The connecting lip 28 is used to connect the patch or the rectangular field 24, which can be arranged on a surface of the bioreactor plant, to the connecting unit 24 and/or to a transmitter cable. The connecting lip 28 in this case remains flexible and is therefore in particular not arranged on, in particular fixed and/or glued to, the surface of the bioreactor plant. The connecting lip 28 permits readily connecting and/or removing the connector or the connecting unit 24. The connecting lip 28 can also be used to bring the specified base capacitance of the patch sensor unit $10_A$ into a desired range by lengthening the conductive paths of the patch sensor unit.

The connecting lip 28 can potentially be sensitive; in other words, this means it can contribute toward a change in the permittivity or capacitance being generated and/or measured. A permittivity change behind the lip can in particular contribute toward the measured capacitance and therefore to the total signal of the sensor.

Because the connecting lip 28 may not have a substantially defined position because it is preferably not glued to the surface of the bioreactor plant, false positive signals can be generated when the connecting lip 28 is moved during the course of the process (for example by tensile forces on the cable or by pressure variations in the bioreactor). However, gluing on the connecting lip 28 does not represent a preferred embodiment because the connecting lip 28 would then no longer be flexible or movable, and because the connecting lip 28 would also readily come detached by cable movement.

A spacer 28a of the sensitive surface, which at least partially encloses and/or covers the connecting lip 28, can serve to reduce or even avoid such undesired effects, such as measuring a false positive signal. The spacer 28a can in particular be a jacket that for example consists of or comprises polypropylene (PP). Alternative shielding substances with a low $\varepsilon_r$, in particular plastics or foams are likewise conceivable.

The spacer 28a can in particular have a thickness of approximately 0.2 mm to approximately 3 mm, preferably from approximately 0.8 mm to approximately 1.3 mm, and particularly preferably from approximately 1 mm. A thickness of approximately 1 mm permits a high flexibility of the connecting lip 28, while at the same time ensuring sufficient distance from potential foreign bodies to prevent a signal coupling in the sensitive areas of the connecting lip.

Figure 2A:
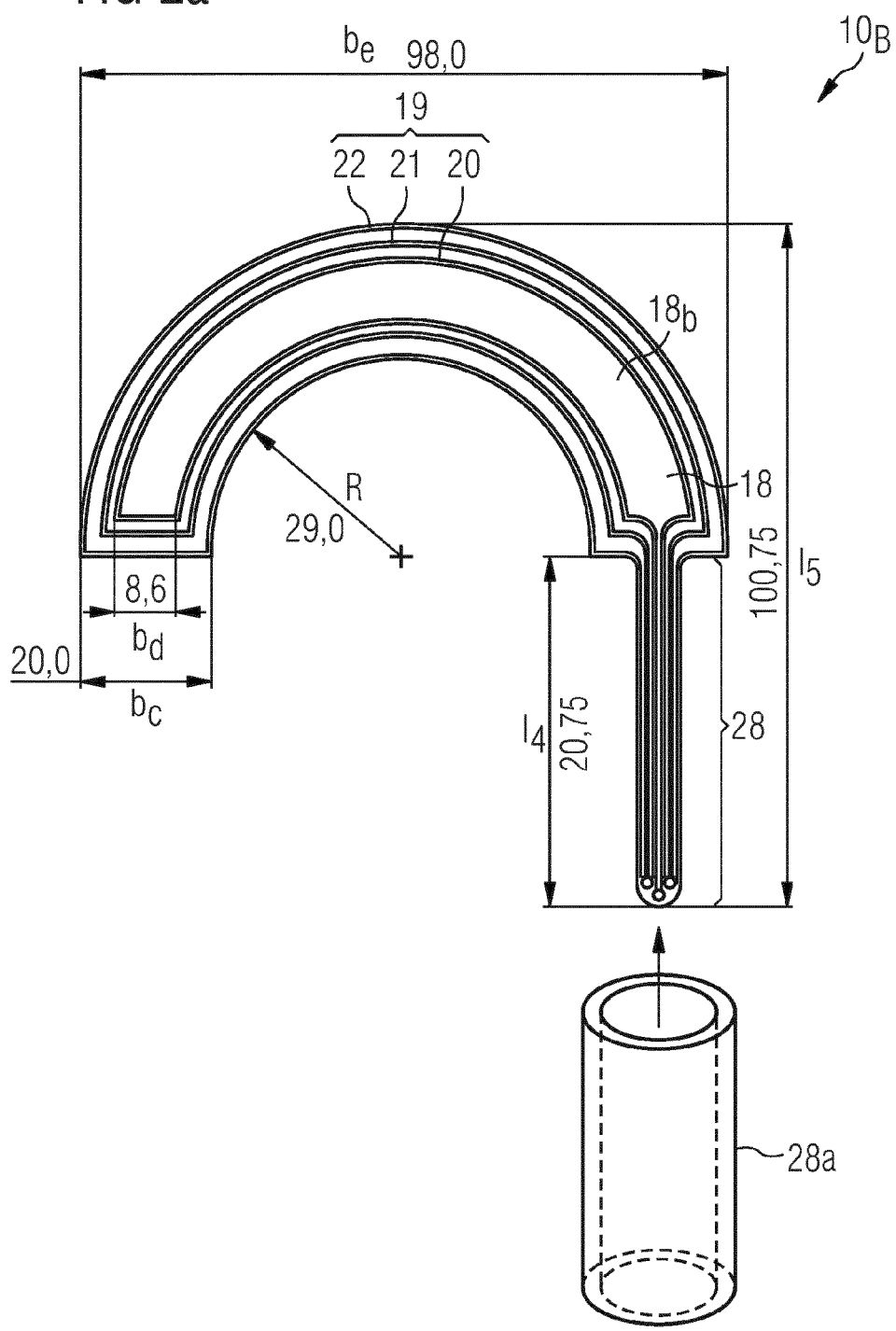
FIG. 2a is a schematic representation of an exemplary arc sensor unit.
Figure 2B:
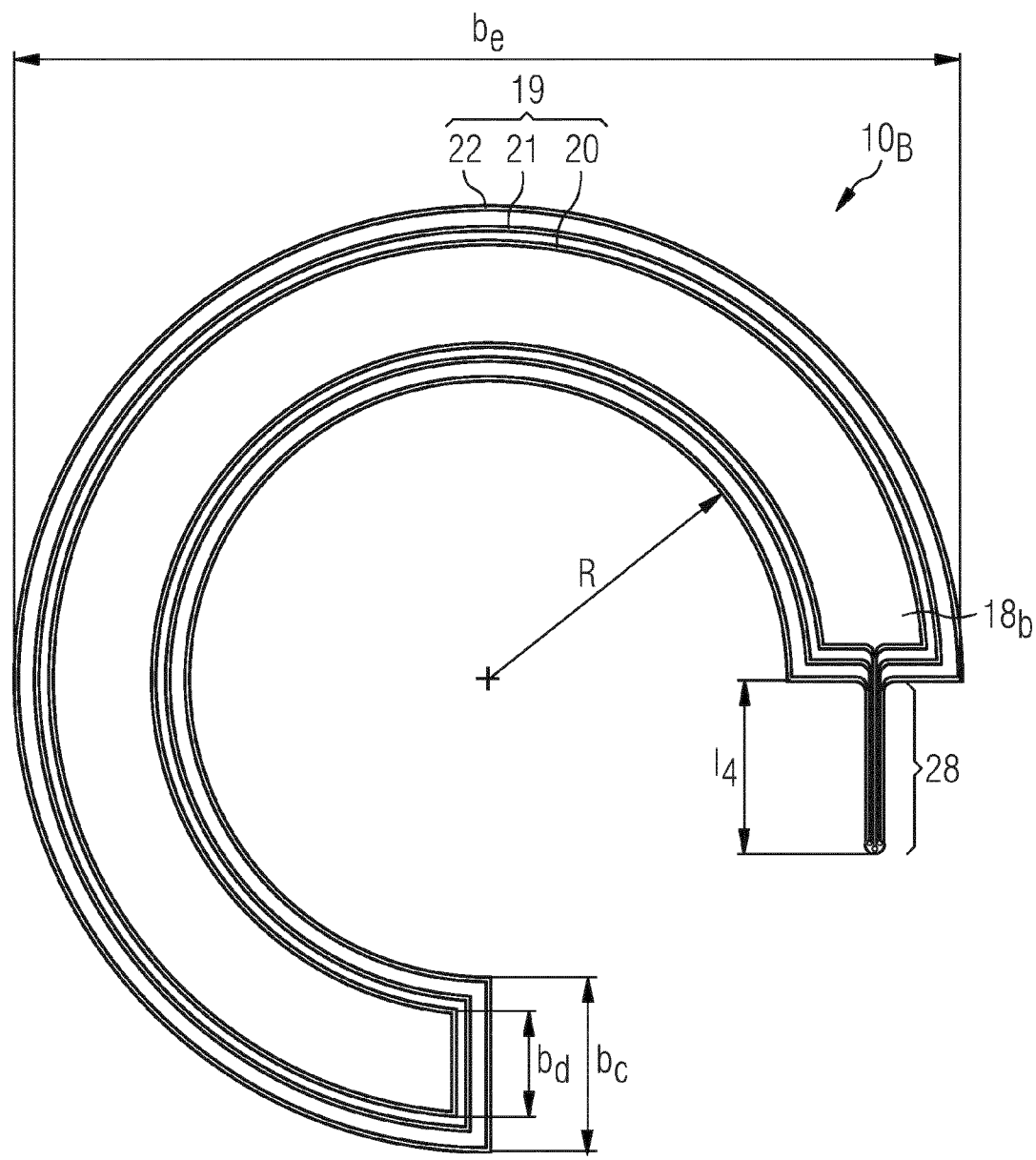
FIG. 2b is a schematic representation of a further exemplary arc sensor unit.

FIGS. 2a and 2b are schematic representations of two exemplary capacitive arc sensor units $10_B$. The features described for the capacitive patch sensor unit $10_A$ can also apply in the capacitive arc sensor units $10_B$, provided they can be combined with it. FIG. 2a is a representation of an exemplary capacitive arc sensor unit $10_B$ having an arc section $18_b$ that substantially corresponds to a semicircular arc.

In the present case, the arc section $18_b$ is in particular used to arrange an electrode system 19. The function of the arc section $18_b$ at least partially corresponds to the function of the rectangular field $18_a$ in a patch sensor unit $10_A$. The arc section $18_b$ can likewise have an adhesive strip 18 or an adhesive gluing field.

The capacitive arc sensor unit $10_B$ has an electrode system 19 that is arranged on the arc section $18_b$ and on the connecting lip 28 of a sensor section 25. The electrode system 19 comprises a sensor electrode 20, a protective electrode 21 and preferably a mass electrode 22. The electrodes 20, 21, 22 at least partially mimic the shape of the capacitive arc sensor unit $10_B$, in particular the arc shape of the arc section $18_b$, in that they are each arranged along the edges of the capacitive arc sensor unit $10_B$ and each form a closed loop.

Alternatively, in particular in the capacitive arc sensor unit $10_B$, the electrode system 19 can in general—that is to say in all embodiments—also be formed as a two-electrode system instead of as a three-electrode system, and then only has a sensor electrode 20 and a protective electrode 21 and no mass electrode 22.

A spacer 28a is shown as a schematic representation. The spacer 28a can at least partially be arranged over the connecting lip 28 such that it at least partially envelops the latter.

The capacitive arc sensor unit $10_B$ can generally be sized arbitrarily. An overall length $I_5$ of the capacitive arc sensor unit $10_B$ including the connecting lip 28 of the sensor section 25 can in particular be selected such that it is between approximately 1 cm and approximately 20 cm, in particular between approximately 5 cm and approximately 15 cm, and preferably between approximately 8 cm and approximately 12 cm. In the exemplary case described here, the overall length $I_5$ is approximately 100.75 mm, or approximately 10 cm.

An overall width be of the capacitive arc sensor unit $10_B$ between the two outer edges of the capacitive arc sensor unit $10_B$ can in particular be selected such that it lies between approximately 1 cm and approximately 15 cm, in particular between approximately 5 cm and approximately 13 cm, and preferably between approximately 8 cm and approximately 12 cm. In the exemplary case described here, the overall width be is approximately 98 mm, or approximately 9.8 cm.

An overall width $b_c$ of the arc-shaped strip of the capacitive arc sensor unit $10_B$ between the two outer edges of the strip can in particular be selected such that it lies between approximately 0.2 cm and approximately 5 cm, in particular between approximately 1 cm and approximately 4 cm, and preferably between approximately 1.5 cm and approximately 3 cm. In the exemplary case describes here, the width $b_c$ of the arc-shaped strip of the capacitive arc sensor unit $10_B$ is approximately 20 mm, or 2 cm.

A minimum width $b_d$ of the arc that mimics the electrodes can in particular be selected such that it lies between approximately 0.1 cm and approximately 1.5 cm, in particular between approximately 0.4 cm and approximately 1.2 cm, and preferably between approximately 0.6 cm and approximately 1.0 cm. In the exemplary case described here, the minimum width $b_d$ of the arc is approximately 8.6 mm, or 0.86 cm.

A length $I_4$ of the connecting lip 28 of the sensor section 25 can in particular be selected such that it ranges between approximately 0.1 cm and approximately 3.5 cm, in particular between approximately 1 cm and approximately 2.5 cm, and preferably between approximately 1.5 cm and approximately 2.3 cm. In the exemplary case described here, the length $I_4$ of the connecting lip 28 of the sensor section 25 is approximately 20.75 mm, or approximately 2.1 cm.

In the case described here, the capacitive arc sensor unit $10_B$ has an arc section 18b having a uniform radius R that can lie between approximately 0.8 cm and approximately 10 cm, in particular between approximately 1.3 cm and approximately 5 cm, and preferably between approximately 1.8 cm and approximately 2.4 cm. In the example shown, the radius R is approximately 29 mm, or approximately 2.9 cm. The arc section $18_b$ can alternatively also have a variable radius, which would for example be the case for an ellipse shape.

The arc of an arc section $18_b$ generally has a curved shape. The curved shape can be described by at least one curve radius r. The arc can substantially have the shape of at least a section of a circular arc, for example approximately that of a quarter, one third, one half, two thirds, or of a three-quarter circular arc, or even that of a full circular arc. Alternatively, the arc can at least substantially correspond to a section of an arc deviating from a circular arc, for example that of an ellipse arc. Other arc shapes having an irregular radius r are likewise conceivable.

FIG. 2b is an exemplary representation of a capacitive arc sensor unit $10_B$ having an arc section $18_b$ that substantially has more than 180° of a circular arc, and in particular substantially corresponds to a three-quarter circular arc. In other words, the arc section $18_b$ approximately corresponds to 270° of a circular arc. The sizing already described for the exemplary capacitive arc sensor unit $10_B$ in FIG. 2a can correspondingly also be applied for the present exemplary capacitive arc sensor unit $10_B$ in FIG. 2a.

Figure 3:
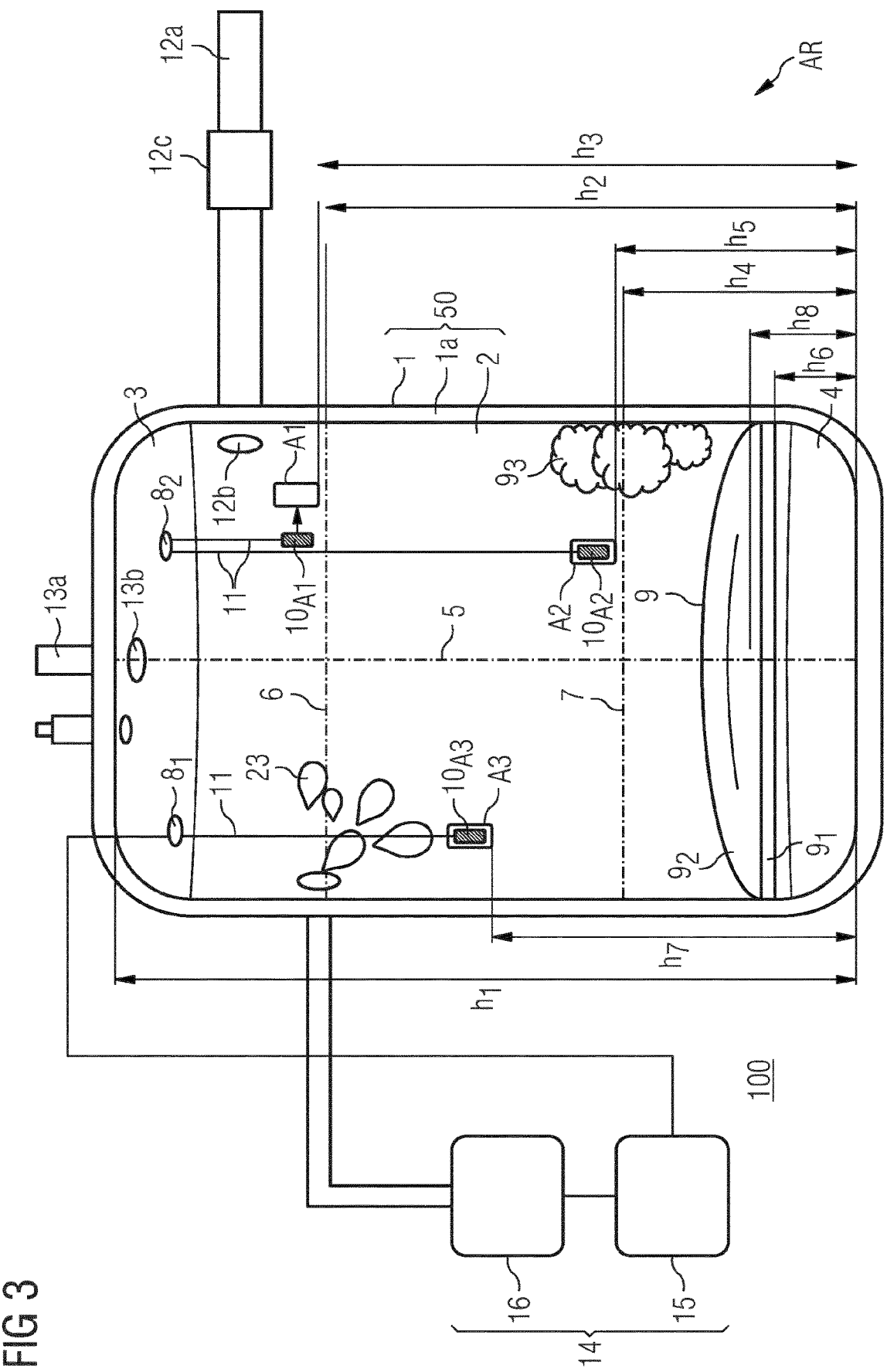
FIG. 3 is a schematic representation of an exemplary bioreactor plant, shown with a schematic cross-section to provide a view into the interior of the container.

FIG. 3 is a schematic representation of a system 100 for detecting foam or a foamy medium $9_2$, $9_3$. An exemplary bioreactor plant 50 is in particular shown with a schematic section or cross-section to provide a view into the interior of the single-use container 1. The container envelope can in particular be or comprise a plastic foil. The plastic foil can in particular comprise at least one of the following materials: Polyolefines, in particular Polyethylene (PE) or Polypropylene (PP), Polyvinylchloride (PVC), Polystyrol (PS), various Polyesters and Polycarbonate (PC) and Polyethyleneterephthalat (PET).

A medium or a bioreactor media filling 9 is positioned in the container interior 2 above the container inner floor 4. The bioreactor media filling 9 can comprise a liquid medium 9 on which a foam $9_2$ has formed. Additionally or alternatively, a foam $9_3$ can also be present on the interior container envelope 1a, wherein the foam either formed there and/or remained attached on the interior container envelope 1a during the fill level change. A foam $9_3$ can in particular also form in and/or on an exhaust hose 12a and/or on another tube or hose. A foam can for example also enter a tube 13a that can act as an upper inlet and is arranged on a corresponding port 13b of the container inner ceiling 3.

In order to have the ability to detect the presence of foam $9_2$, $9_3$, at least two, in particular three capacitive patch sensors $10_{A1}$, $10_{A2}$, $10_{A3}$ are correspondingly arranged on the interior container envelope 1a at respectively different situating positions, in particular at the situating positions A1, A2, A3. A first capacitive patch sensor unit $10_{A1}$ is arranged just in the proximity slightly above a limit line 6 that indicates the maximum fill level. The arrow indicates the direction in which the first capacitive patch sensor unit $10_{A1}$ is arranged at the situating positions A1. A second capacitive patch sensor unit $10_{A2}$ is arranged in the proximity slightly above a limit line 7 that indicates or corresponds to the minimum fill level. A third capacitive patch sensor unit $10_{A3}$ is arranged between the limit lines 7, 8.

The term "slightly above" refers to a distance between the respectively stated height and the lower edge of the sensor unit, said distance being between approximately 0.2 cm and approximately 10 cm, in particular between 0.5 cm and 5 cm, and preferably between approximately 1 cm and 3 cm.

At least a part of the capacitive patch sensor units $10_{A1}$, $10_{A2}$, $10_{A3}$ can alternatively also for contactless measurement be arranged on the exterior container envelope 1b. Additional sensor units can in particular also be arranged on the bioreactor plant 50 for detecting the foam level. The arrangement of the capacitive patch sensor units $10_{A1}$, $10_{A2}$, $10_{A3}$ is in particular suited to determine whether a medium 9, in particular a foam $9_2$, $9_3$ is present at a tolerable level between the minimum and the maximum fill level, or whether, potentially in particular foam $9_2$, $9_3$ grows above the limit line 6 that indicates the maximum fill level, and can potentially enter one of the tubes 12a, 13a.

The limit line 7 that indicates the minimum fill level is designed to indicate whether the single-use container 1 is sufficiently filled with a medium 9, in particular a liquid medium $9_1$, which would in particular be the case when the height $h_6$ of the fluidic medium $9_1$ were approximately at the height of the limit line 7. The limit line 6 that indicates the maximum fill level is designed to indicate whether the single-use container 1 is filled to a maximum with a medium 9, in particular a liquid medium $9_1$, which would in particular be the case when the height $h_6$ of the fluidic medium $9_1$ or the height $h_6$ of the foam sitting above it were approximately at the height of the limit line 6. A height in this case corresponds to a distance from a container inner floor 4 to the maximum height of the foam $9_2$, $9_3$ or of the fluidic medium $9_1$.

The distance from the container inner floor 4 to the limit line 7 corresponds to the height $h_4$ and the distance from the container inner floor 4 to the limit line 6 corresponds to the height $h_2$. The distance from the container inner floor 4 to the bottom edge of the first patch sensor unit $10_{A1}$ corresponds to the height $h_3$. The distance from the container inner floor 4 to the bottom edge of the second patch sensor unit $10_{A2}$ corresponds to the height $h_5$. The distance from the container inner floor 4 to the bottom edge of the third patch sensor unit $10_{A3}$ corresponds to the height $h_7$. The distance from the container inner floor 4 to the container inner ceiling 3 corresponds to the height $h_1$.

One of the capacitive sensor units $10_{A1}$, $10_{A2}$, $10_{A3}$ is preferably designed to be switched off or disabled. In particular, a capacitive sensor unit $10_{A2}$ that is arranged at a situating position A2 in the bottom third of the bioreactor plant 50 is designed to be switched off. A patch sensor unit $10_{A1}$, $10_{A2}$, $10_{A3}$ and/or an arc sensor unit $10_B$ can be switched off.

The system 100 is optionally designed to switch off one of the capacitive sensor units $10_{A1}$, $10_{A2}$, $10_{A3}$. In particular, the system 100 is designed to switch off a capacitive sensor unit $10_{A2}$ that is arranged at a situating position A2 in the bottom third of the bioreactor plant 50.

Likewise, several capacitive sensor units $10_{A1}$, $10_{A2}$, $10_{A3}$ can be switched off, depending on up to what level the bioreactor plant 50 is filled or what fill level the medium has within the bioreactor plant 50. Different fill levels for different processes can be reached within the bioreactor plant 50 in particular on fed batch processes. This would have the consequence that one or several capacitive sensor units $10_{A1}$, $10_{A2}$, $10_{A3}$ would detect a medium instead of the presence or absence of a foam, resulting in a misinterpretation of the recorded data. It can therefore for example be erroneously assumed that a foam is present in the immediate environment of a capacitive sensor unit $10_{A1}$, $10_{A2}$, $10_{A3}$, because the latter detects a change in permittivity caused by filling with the medium. For this purpose, the bioreactor plant 50, the system 100 or the capacitive sensor unit $10_{A1}$, $10_{A2}$, $10_{A3}$ can be designed to automatically and/or manually switch off or disable the respective capacitive sensor unit $10_{A1}$, $10_{A2}$, $10_{A3}$. "Switching off" in this case means that no state is detected, but at a minimum that no data are forwarded by the respectively switched off capacitive sensor unit $10_{A1}$, $10_{A2}$, $10_{A3}$.

The capacitive patch sensor units $10_{A1}$, $10_{A2}$, $10_{A3}$ are connected to a monitoring unit 14 by a cable 11, for example to transfer data, to be controlled, and/or to be supplied with power. Data can alternatively also be transmitted wirelessly. The cables 11 are in this case respectively guided through a cable port $8_1$, $8_2$ from the container interior 2 to the container exterior AR.

Figure 4:
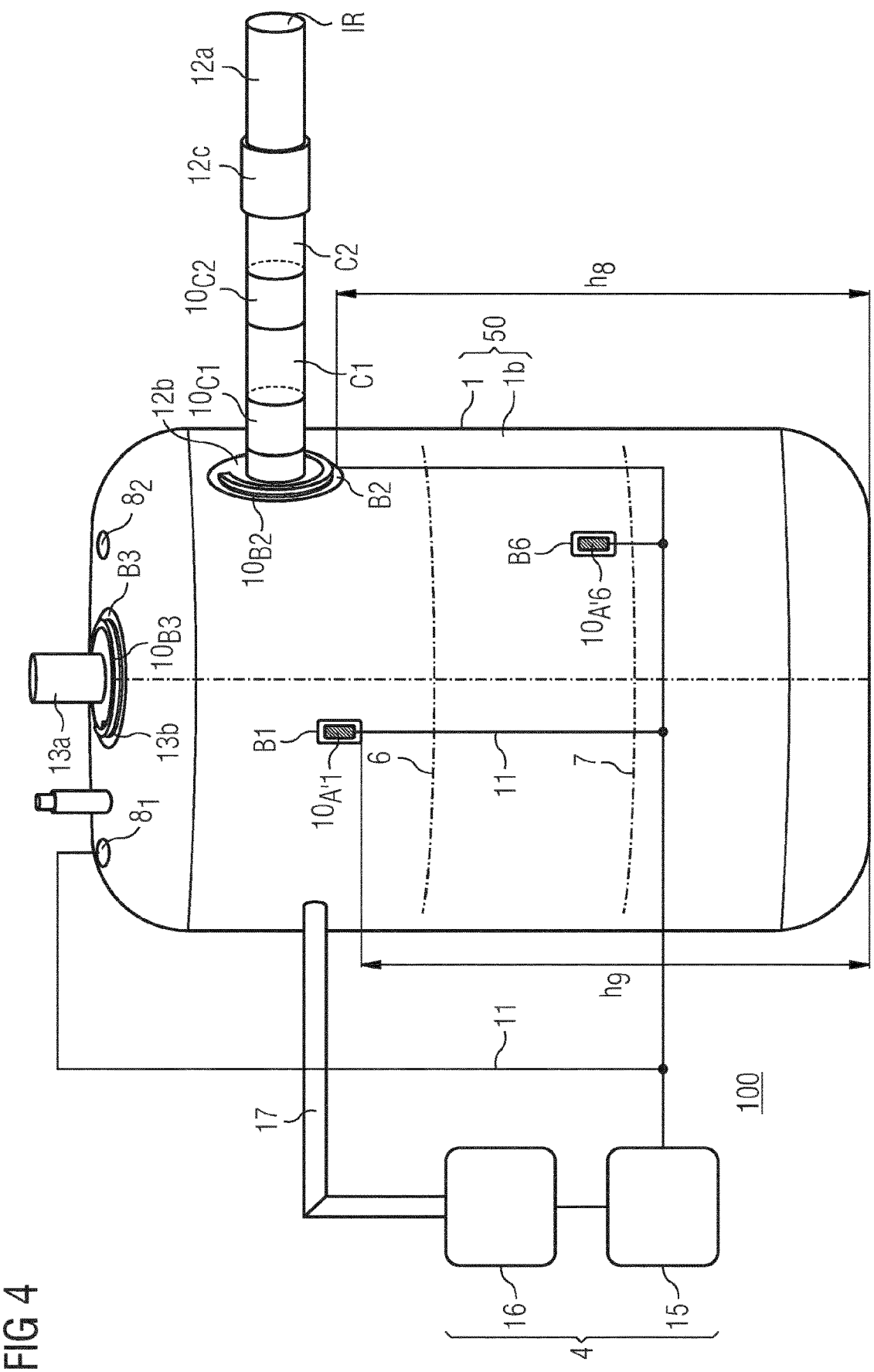
FIG. 4 is a schematic representation of an exemplary bioreactor plant as seen from the outside.

FIG. 4 is a schematic representation of an exemplary bioreactor plant 50 from FIG. 3 as seen from the outside. Two capacitive arc sensor units $10_{B2}$, $10_{B3}$ are arranged from the exterior AR of the bioreactor plant 50 on the exterior container envelope 1b at the situating positions B2, B3. Further patch sensor units $10_{A1'1}$, $10_{A'6}$ are likewise arranged on the exterior container envelope 1b at the situating positions B1, B6. The patch sensor unit $10_{A'1}$ is for example arranged at the situating position B1 at the height $h_9$ above the limit line 6 and below the port 12b of the exhaust hose 12a to detect the presence of a foam level that can potentially enter the exhaust hose 12b without taking an action to counteract foam formation.

The patch sensor units $10_{A'1}$, $10_{A'6}$ are designed to contactlessly and/or through the container wall detect a foam level within the bioreactor plant 50, in particular within the single-use container 1. When patch sensor units $10_{A1}$, $10_{A2}$, $10_{A3}$ are arranged in the container interior 2, the patch sensor units $10_{A'1}$, $10_{A'6}$ on the exterior container envelope 1b can be optional. Otherwise, two or more patch sensor units on the exterior container envelope 1b can be an alternative to the patch sensor units $10_{A1}$, $10_{A2}$, $10_{A3}$ on the exterior container envelope 1b.

The capacitive arc sensor units $10_{B2}$, $10_{B3}$ are designed to detect the presence of foam $9_2$, $9_3$ at critical positions B2, B3. An arc sensor unit $10_{B2}$ is for example arranged on a port 12b of the exhaust hose 12a at the situating position B2 in order to detect in this manner whether foam $9_2$, $9_3$ is entering the exhaust hose 12a. In the same manner, it can for example be prevented that foam $9_2$, $9_3$ blocks and/or contaminates a filter 12c on the exhaust hose 12a.

At least one, in particular two (further) sensor units, that is to say two collar sensor units $10_{C1}$, $10_{C2}$ are arranged on the exterior on the exhaust hose 12a, each on one or several situating positions C1 and C2. The collar sensor unit $10_{C1}$/$10_{C2}$ is preferably a capacitive sensor unit, similar to the patch sensor unit $10_A$ and or the arc sensor unit $10_B$.

The collar sensor unit $10_{C1}$ is in particular arranged directly or immediately behind port 12b at the situating position C1 at the exhaust hose 12a. This collar sensor unit $10_{C1}$ can detect whether foam $9_2$, $9_3$ has entered the interior IR of the exhaust hose 12a. The collar sensor unit $10_{C1}$ can just like the collar sensor unit $10_{C2}$ be a (preferably substantially rectangular) strip or a (preferably substantially rectangular) patch that is, or can be, placed in particular along its length axis at least partially about the circumference of a hose and/or a tube or line, thus forming a collar around the circumference of the tube. In other words, the shape of this sensor unit is preferably that of a strip that is at least partially taped with its surface around the hose. The collar sensor units $10_{C1}$ and/or $10_{C2}$ in particular form an arc when they are placed around the hose or the tube or the line, wherein they for example merely represent a (preferably substantially rectangular) sensor unit prior to being placed around the hose or the tube or the line.

A collar sensor unit $10_{C1}$ and/or $10_{C2}$ can generally be designed to envelop at least substantially half, preferably at least substantially two thirds, and particularly preferably substantially three quarters of the circumference of a tube and/or a hose. Prior to being placed onto the hose and/or tube, the collar sensor unit $10_{C1}$ and/or $10_{C2}$ for example has the shape of a patch sensor unit, or is at least similar to this shape. In other words, prior to being placed or attached onto a tube or a line, the collar sensor unit $10_{C1}$/$10_{C2}$ substantially has no curvature, and in particular has a substantially two-dimensional planar surface that forms a flat plane.

When at least partially enveloping a tube or a line, the collar sensor unit $10_{C1}$/$10_{C2}$ assumes a curved shape, resulting not in a flat plane but in a curved surface whose curvature is in particular determined by the radius of the tube. The collar sensor unit is preferably placed around the tube or line with its length axis, substantially vertically to the length axis of the tube or line. The curvature of the collar sensor unit $10_{C1}$/$10_{C2}$ is in this case substantially coaxial to the length axis (of at least a part) of the tube or line. Alternatively, the collar sensor unit $10_{C1}$/$10_{C2}$ can also be placed onto the tube or line in an "oblique" orientation, meaning that the length axis of the collar sensor unit $10_{C1}$/$10_{C2}$ is not vertical in relation to the length axis of the tube or line.

All sensor units, and therefore also the sheet and patch sensor units, can principally all have a curvature that is substantially determined by the radius of the element on which they are placed. But this radius is generally greater than on a collar sensor unit $10_{C1}$/$10_{C2}$ because the collar sensor unit $10_{C1}$/$10_{C2}$ is generally placed onto tubes or lines and not on the container of a bioreactor plant. The curvature of the collar sensor unit $10_{C1}$/$10_{C2}$ is for this reason generally more pronounced than on the arc sensor unit $10_B$ or the patch sensor unit $10_A$.

This curvature, which results from the fact that the sensor units $10_A$ $10_B$, $10_C$ are flexible and can be placed onto the (preferably exterior) shape of a surface, such as that of a single-use container or bioreactor 1 is not to be confused with the curvature of the arc of an arc sensor unit $10_B$. The arc of an arc sensor unit $10_B$ can lie in a two-dimensional plane, in particular when the arc sensor unit $10_B$ was not yet arranged on the system 100 or the container 1.

In other words, an arc sensor unit $10_B$ already has an arc in its two-dimensional form, wherein the latter lies in a plane before it is arranged on a bioreactor plant 100 or a container 1. If the surface onto which the arc sensor unit $10_B$ will be arranged corresponds to a flat plane without arc, the arc sensor unit $10_B$ can be at least partially arranged around a port (such as port 12b) without its surfaces assuming a curvature. The collar sensor unit 10c by contrast always has a curvature when it is arranged on a hose or tube or a line.

The distance between Port 12b and situating position C1 is for example between approximately 2 cm and approximately 30 cm, in particular between approximately 5 cm and approximately 15 cm, and preferably between approximately 7 cm and approximately 12 cm. The further collar sensor unit $10_{C2}$ is arranged directly upstream of filter 12c at the situating position C2 on the exhaust hose 12a. This collar sensor unit $10_{C2}$ can detect whether foam $9_2$, $9_3$ has already entered the interior IR of the exhaust hose 12a, that is to say in the immediate vicinity of filter 12c. The distance between filter 12c and situating positions C2 is for example between approximately 2 cm and approximately 30 cm, in particular between approximately 5 cm and approximately 15 cm, and preferably between approximately 7 cm and approximately 12 cm.

The exhaust hose 12a is arranged at a comparatively high position, for example in the upper half, in particular in the upper third, and preferably in the upper quarter of the single-use container 1. The distance between the container inner floor 4 and the bottom edge of port 12b for the exhaust hose 12a corresponds to the height $h_8$.

A further arc sensor unit $10_{B3}$ is arranged on the port 13b for the upper inlet 13a in order to detect at this situating position B3 whether a foam has entered, or will enter, the hose of the upper inlet 13a.

The capacitive arc sensor units $10_{B2}$, $10_{B3}$ are connected to the monitoring unit 14 by cable 11. The computing unit 15 of the monitoring unit 14 can in this case receive and analyze and/or process data, and forward the data to the open-loop and/or closed-loop control unit 16 such that the open-loop and/or closed-loop control unit 16 can initiate an action, in particular when a critical state is detected. The open-loop and/or closed-loop control unit 16 can for example initiate an action to add an anti-foaming agent 23 to the container interior 2 through a hose 17, such that foam formation can be reduced and/or suppressed. Several ports can in particular be arranged on the bioreactor plant 50, such that an anti-foaming agent 23 can be locally deployed at the place where a foam $9_2$, $9_3$ is present.

Actions can at least one be one of the following: Trigger a visible and/or audible alarm, trigger the addition of anti-foaming agent 23, stop the addition of anti-foaming agent 23, switch off any foam-forming apparatus, for example switch off a mixing device and/or switch off a substance addition.

Figure 5:
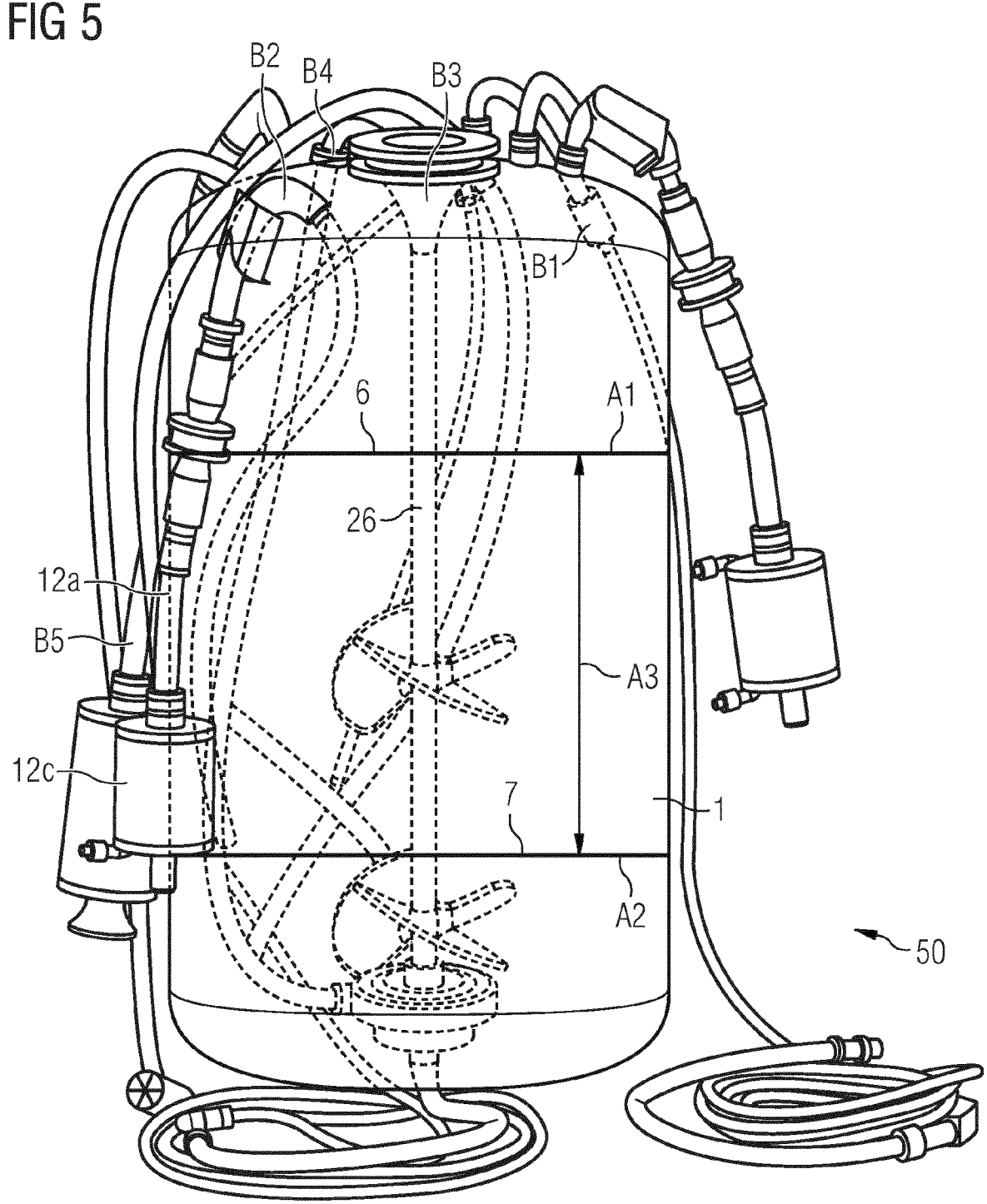
FIG. 5 is a realistic representation of an exemplary bioreactor plant as seen from the outside.

FIG. 5 is a realistic representation of an exemplary bioreactor plant 50 as seen from the outside. The bioreactor plant 50 in particular has a single-use container 1 that represents a single-use bag. The bioreactor plant 50 also has a mixing unit 26 for stirring or mixing a medium. In addition to several hoses, the bioreactor plant 50 has an exhaust hose 12a with a filter 12c. The illustration indicates a minimum fill level 7 and a maximum for level 6 using marking lines. The illustration further indicates the situating positions A1, A2 and A3 at which patch sensor units can be preferably arranged. In particular the foam level can be monitored at these situating positions A1, A2 and A3. The illustration also shows situating positions B1, B2, B3, C1, C2 at which preferably arc sensor units (or other types of sensor units, such as a patch sensor unit $10_{A1}$ or a collar sensor unit $10_{C1}$, $10_{C2}$) can be arranged. In particular, a critical state can be detected at these situating positions B1, B2, B3, C1, C2, for example when a foam is present in the vicinity of a report, in particular in the vicinity of the port for the exhaust hose 12a or even in the vicinity of the filter 12c.

The maximum fill level 6 is in particular a predetermined value for the recommended maximum filling with a medium, which is for example indicated by a fill level marking on and/or in the bioreactor plant, in particular on and/or in the single-use container. The minimum fill level 7 is in particular a predetermined value for the recommended minimum filling with a medium, which is for example indicated by a fill level marking on and/or in the bioreactor plant, in particular on and/or in the single-use container.

Safe and reliable operation of the bioreactor plant is in particular recommended for filling with a medium within the limits between approximately the maximum fill level 6 and approximately the minimum fill level 7.

The respective situating positions can in particular be drawn or marked on the corresponding bioreactor plant such that the user can readily arrange the sensor unit at the corresponding situating positions.

A capacitive patch sensor unit in particular has at least one adhesive strip or at least one adhesive strip that for example substantially has a rectangular or circular shape. A capacitive patch sensor unit can in particular be similar to the shape of a medical patch. A substantially rectangular adhesive strip for example has a length and/or a width of respectively approximately 0.5 cm to approximately 10 sent is, in particular from approximately 1.5 cm to approximately 7 cm, and preferably from approximately 2 cm to approximately 5 cm.

The measurement surface and/or the taping surface of the adhesive strip of capacitive sensor units, preferably of capacitive patch sensor units, in particular has a geometrically substantially "non-eccentric" design. Advantageous surface shapes can for example be substantially circular, square, rectangular. On substantially rectangular measurement surfaces, a preferred edge length ratio is a value of approximately less than 2, such as approximately 1 for substantially square services, or approximately 1.5 or approximately 0.5 rectangular surfaces that are not square in shape.

A capacitive arc sensor unit in particular at least partially has a substantially round shape, in particular a circular arc shape. The capacitive arc sensor unit can for example have the shape of a semicircular arc. The shape in this case in particular has a curved strip that has a width of approximately 0.3 cm to approximately 10 cm, in particular from approximately 1 cm to approximately 7 cm, and preferably from approximately 1.5 cm to approximately 3 cm, such that the capacitive arc sensor unit can for example envelop a port. The radius of a circular arc of a capacitive arc sensor unit sensor unit can in particular lie between approximately 0.5 cm and approximately 10 cm, in particular between approximately 1 cm and approximately 7 cm, and preferably between approximately 1.5 cm and approximately 3 cm. The capacitive arc sensor unit in particular has a substantially straight connection section.

A sensor unit is in particular a capacitive single-use sensor unit for substantially single use arrangement on a bioreactor plant. Alternatively, the capacitive sensor unit can also be a capacitive multi-use sensor unit that is designed to be arranged on a bioreactor plant multiple times.

A sensor unit can be a so-called "fill level switch". Measurements using capacitive switches detect a change of the dielectric constant Cr, and said change is then converted into a control signal. The advantage of this technology is that the medium can for example be detected behind a dielectric container wall.

Figure 6:
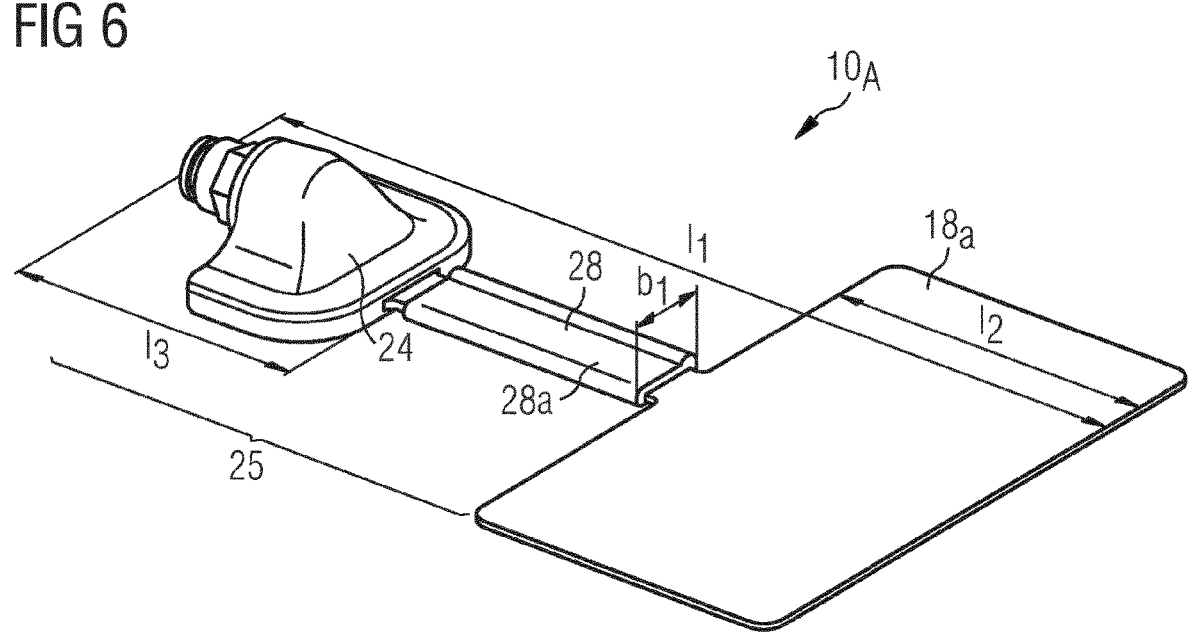
FIG. 6 is a schematic perspective representation of an exemplary patch sensor unit.

FIG. 6 is a schematic perspective representation of an exemplary capacitive patch sensor unit $10_A$ [attached spacer].

The capacitive patch sensor unit $10_A$ has a connection section 25 having a connecting unit 24 and a connecting lip 28. The connecting lip 28 represents a substantially elongated connecting section, in particular an electrically conductive path to supply the electrode system 19 with power, and on whose one end the rectangular field $18_a$ is located, and on whose other end the connecting unit 24 is located. The connecting unit 24 for example is used for signal transmission and/or power supply. By applying alternating current, an electrical alternating field can be generated in this manner in the electrode system 19, and the resulting current flow can be detected as a signal.

A connecting lip 28 is advantageous to maintain the flexibility of the connection or of the connection section between the rectangular field $18_a$ of the patch sensor unit $10_A$ and the transmitter cable (not shown) that is, or can be, connected to the connecting unit 24. In other words, a substantially flexible connecting lip 28 is provided between the connecting unit 24 and the rectangular field $18_a$ of the patch sensor unit $10_A$. Provided the connecting unit 24 is removable or detachable, the connecting unit 24 can then also be readily connected to, or disconnected from, the rectangular field $18_a$ of the patch sensor unit $10_A$. The connecting lip 28 is also advantageous to bring the specified base capacitance of the patch sensor unit $10_A$ into a desired range by lengthening the conductive paths of the patch sensor unit.

The connecting lip 28 in particular does not have a defined—or permanently constant and pre-determined—position, as is for example preferably the case with the rectangular field $18_a$ of the patch sensor unit $10_A$ because the connecting lip 28 is preferably not taped to the container. As a result, undesirable interference signals, such as false positive signals, can be generated and detected by the electrode system, in particular when the connecting lip 28 is moved during the course of the process, for example by tensile forces on the cable or pressure fluctuations in the bioreactor.

However, the connecting lip 28 should not be fixed to the container with restricted movement, and should in particular not be taped, because the connecting lip 28 in this case does not provide the required flexibility and freedom of motion, and the connecting lip 28 could potentially also at any rate easily come detached due to cable movement. Interference signals can then in particular not be prevented or reduced by fixing, in particular taping, the connecting lip 28 to the container.

The spacer 28a is preferably provided on the sensitive surface, in particular on the connecting lip 28. The spacer 28a in particular is a jacket made of Polypropylene. Other plastics can alternatively also be used. This has the advantage that previously described interference signals can be reduced or even avoided.

The material of the spacer can preferably at least partially have a thickness of approximately 1 mm, firstly in order to be substantially flexible, and secondly to ensure a sufficiently large distance from potential foreign bodies to the sensitive region of the connecting lip.

The spacer 28a in particular covers a major part of the sensitive surface. The spacer 28a can be aligned by a tab on an over-molding of the connector. The locking mechanism is preferably reversibly lockable such that the spacer can be used multiple times. The spacer has rounded or deburred edges in particular to avoid cutting into a single-use container, and additionally a thin area such that the spacer can be designed as a single part and can envelop the connecting lip 28 like a strap.

The disclosure therefore in particular relates to a capacitive patch sensor unit $10_A$ having:
- a field, in particular a rectangular field $18_a$ for attaching on a surface;
- an electrode system 19 that is at least partially arranged on the field and that is designed to detect changes of permittivity and/or capacitance in the immediate vicinity or environment, and in particular for capacitive measurements at one of the situating positions of the bioreactor plant 50 and for detecting the presence of foam $9_2$, $9_3$ at the situating position A1-A3; B1-B6 based on the capacitive measurement;
- a connecting lip 28 to electrically connect a power supply to the electrode system; and preferably
- a spacer 28a designed to at least partially envelop or cover the connecting lip 28.

The disclosure also in particular relates to a capacitive arc sensor unit $10_A$ having:
- a field, in particular an arc section $18_b$ for attaching to a surface;
- an electrode system 19 that is at least partially arranged on the field and that is designed to detect changes of permittivity and/or capacitance in the immediate vicinity or environment, and in particular for capacitive measurements at one of the situating positions of the bioreactor plant 50 and for detecting the presence of foam $9_2$, $9_3$ at the situating position A1-A3; B1-B6 based on the capacitive measurement;
- a connecting lip 28 to electrically connect a power supply to the electrode system; and preferably
- a spacer 28a designed to at least partially envelop or cover the connecting lip 28.

In general, a sensor field can have a field of any conceivable shape, wherein the field can be attached to a surface of the bioreactor plant. Such a sensor unit can have a connecting lip and a spacer, entirely independently of the shape of said field. The connecting lip is in particular designed such that it is not fixed and/or taped to the surface of the bioreactor plant. The connecting lip connects an electrode system arranged on the field to a connecting unit, preferably electrically.

| | |
|---|---|
| 1 | Single-use container of a bioreactor |
| 1a | Interior container envelope |
| 1b | Exterior container envelope |
| 2 | Container interior or interior of the single-use container |
| 3 | Container inner ceiling |
| 4 | Container inner floor |
| 5 | Container length axis |
| 6 | Limit line for maximum fill level |
| 7 | Limit line for minimum fill level |
| $8_1$, $8_2$ | Cable port |
| 9 | Medium or bioreactor media filling |
| 9i | Fluidic medium |
| 92 | Foamy medium/foam on fluidic medium |
| 93 | Foamy medium/foam as deposit on the interior container envelope |
| $10_A$ | Capacitive (patch) sensor unit |
| $10_{A1}$, $10_{A2}$, $10_{A3}$ | First, second, and third capacitive patches sensor unit for detecting the level of a foam, in particular from the interior container envelope. |
| $10_{A'6}$, $10_{A'1}$ | Capacitive patches sensor unit for detecting the level of a foam, in particular from the exterior container envelope. |
| $10_B$ | Capacitive (arc) sensor unit |
| $10_{B2}$, $10_{B3}$ | First and second capacitive arc sensor unit for detecting the presence of foam with exterior attachment |
| $10_{C1}$, $10_{C2}$ | Collar sensor units that can be at least partially placed around a tube and/or a hose |
| 11 | Cable |
| 12a | Exhaust hose |
| 12b | Exhaust port or ports for exhaust hose |
| 12c | Filter |
| 13a | Tube or hose upper inlet/outlet |
| 13b | Port for upper inlet/outlet |
| 14 | Monitoring unit |
| 15 | Computing unit |
| 16 | Open-loop and/or closed-loop control unit |
| 17 | Tube or hose for open-loop control and/or closed-loop control of foam formation or the foam level |
| 18 | Adhesive strip |
| $18_a$ | Rectangular field |
| $18_b$ | Arc section |
| 19 | Electrode system |
| 20 | Sensor electrode |
| 21 | Protective electrode |
| 22 | Mass electrode |
| 23 | Substance for reducing and/or preventing foam (foam formation) or anti-foaming agent |
| 24 | Connecting unit |
| 25 | Connection section |
| 26 | Mixing unit |
| 28 | Connecting lip of the sensor section 25 |
| 28a | Spacer |
| 50 | Bioreactor plant |
| 100 | System for detecting at least one presence of foam |

-continued

| | |
|---|---|
| A1, A2, A3 | First, second, and third situating position for a capacitive sensor unit for detecting the level of a foam, in particular from the interior container envelope. |
| AR | Container exterior |
| B1, B2, B3, C1, C2, B6 | First to sixth situating position for a capacitive sensor unit for detecting the presence, in particular the level, of a foam, in particular from the exterior container envelope |
| $b_a$ | Width of the rectangular field |
| $b_b$ | Width of the rectangular field |
| $b_c$ | Width of the strip of the arc section |
| $b_d$ | Minimum width of the arc, of the electrodes |
| $b_e$ | Overall width of the arc section |
| $h_5$ | Height from the bioreactor inner floor to the bottom edge of the second capacitive patch sensor unit $10_{A2}$ |
| $h_6$ | Height from the bioreactor inner floor to the actual fill level of the fluidic bioreactor media filling or the height of the fluid |
| $h_r$ | Height from the bioreactor inner floor to the bottom edge of the third capacitive patch sensor unit $10_{A3}$ |
| $h_a$ | Height from the bioreactor inner floor to the actual fill level of the foamy bioreactor media filling or the height of the foam |
| IR | Hose interior |
| $l_1$ | Overall length, including connection section |
| $l_2$ | Length of the rectangular field |
| $l_3$ | Length of the connecting unit |
| $l_4$ | Length of the connection section |
| $l_5$ | Overall length, including connection section |
| R | Radius |

The invention claimed is:

1. A system for detecting at least the presence of foam of a medium in of a bioreactor plant, wherein the system comprises:
   a bioreactor plant having at least one single-use container for receiving the medium, that can have the foam, and at least one exhaust port; and
   at least two capacitive sensor units, each capacitive sensor unit of the at least two capacitive sensor units being attached at a different situating position of the bioreactor plant, wherein at least one capacitive sensor unit of the at least two capacitive sensor units is arranged:
   (i) at a first situation position in the immediate vicinity of the exhaust port, or
   (ii) at a second situation position on or in spatial proximity to an exhaust hose of the bioreactor system, wherein the exhaust hose is fluidically connected to the exhaust port, or
   (iii) at a third situation at a height below the height of the exhaust port, in particular not in the immediate vicinity of the exhaust port; and
   at least one monitoring unit with at least one open-loop and/or closed-loop control unit, wherein the at least one monitoring unit is configured to switch off a mixer and/or a sparging when the sensor unit arranged at the first situation position or the second situation position or the third situation position is triggered,
   wherein the capacitive sensor units each comprise at least one electrode system for a capacitive measurement and can detect the presence of foam at the situating positions on the basis of the capacitive measurement; and
   wherein the capacitive sensor units are designed to transmit recorded data concerning the presence of foam to the at least one monitoring unit for monitoring, open-loop control and/or closed-loop control of foam formation in the bioreactor plant based on said data.

2. The system according to claim 1, wherein at least one of the capacitive sensor units has an adhesive strip on which the electrode system is at least partially arranged, wherein the adhesive strip is designed such that the at least one capacitive sensor unit can be arranged on the bioreactor plant.

3. The system according to claim 1, wherein at least one of the capacitive sensor units is a capacitive arc sensor unit, wherein the shape of the capacitive arc sensor unit comprises at least a section of an arc, in particular a circular arc.

4. The system according to claim 3, wherein the bioreactor plant has at least one port, in particular a circular port to fluidically connect the interior of the single-use container to another element and/or the exterior of the single-use container, and wherein the at least one capacitive arc sensor unit is designed to at least partially envelop the port.

5. The system according to claim 4, wherein the bioreactor plant has at least one hose and/or a tube fluidically connected to the port, wherein the at least one capacitive arc sensor unit is designed to at least partially envelop the hose and/or the tube.

6. The system according to claim 1, wherein at least one of the capacitive sensor units, in particular a capacitive patch sensor unit is designed to detect the presence of foam, in particular a foam level in the single-use container and is arranged at a situating position in the interior of the single-use container, in particular on an interior container envelope, and wherein the at least one capacitive sensor unit preferably can be, and in particular is, sterilized.

7. The system according to claim 6, wherein the situating position on the interior container envelope is at least one of the following situating positions:
   the situating position in the proximity, preferably at a height slightly above a height, of a predetermined maximum fill level of the single-use container, in particular above a limit line of a predetermined maximum fill level;
   the situating position in the proximity, preferably at a height slightly above a height, of a predetermined minimum fill level of the single-use container, in particular a limit line of a predetermined minimum fill level;
   the situating position at a height between the height of the predetermined minimum fill level and the height of the predetermined maximum fill level, in particular between a limit line of the predetermined minimum fill level and a limit line of the predetermined maximum fill level.

8. The system according to claim 1, wherein at least one of the capacitive sensor units, in particular a capacitive arc sensor unit and/or a collar sensor unit is arranged at a situating position outside of the single-use container, in particular on an exterior container envelope and/or on a port and/or on a hose or a tube or a line.

9. The system according to claim 8, wherein the situating position on the exterior container envelope is at least one of the following situating positions:
   the situating position at a height slightly below the height of an exhaust port of the single-use container, in particular not in the immediate vicinity of the exhaust port;
   the situating position in the immediate vicinity of the exhaust port;
   the situating position in the immediate vicinity of a port for an upper inlet/upper outlet of the single-use container;

the situating position on an exhaust hose of the bioreactor plant, wherein the exhaust hose is fluidically connected to the exhaust port and the situating position is located in the immediate vicinity of the exhaust port;

the situating position on the exhaust hose of the bioreactor plant in the immediate vicinity of a filter of the exhaust hose, in particular between the exhaust port and the filter.

10. A method for detecting at least one presence of foam of a medium, comprising:

Provide a bioreactor plant having at least one single-use container for receiving the medium that can comprise the foam, and at least one exhaust port;

Arrange at least two capacitive sensor units at at least two situating positions of the bioreactor plant, wherein the capacitive sensor units each have at least one electrode system for a capacitive measurement, wherein at least one capacitive sensor unit of the at least two capacitive sensor units is arranged:

(i) at a first situation position in the immediate vicinity of the exhaust port, or (ii) at a second situation position on or in spatial proximity to an exhaust hose of the bioreactor system, wherein the exhaust hose is fluidically connected to the exhaust port, or (iii) at a third situation at a height slightly below the height of the exhaust port, in particular not in the immediate vicinity of the exhaust port; and Record data concerning the presence of foam at the situating positions based on the capacitive measurements; and Transmit the recorded data concerning the presence of foam to a monitoring unit for monitoring foam formation in the bioreactor plant based on the data using the capacitive sensor units;

triggering a measure, including switching off a mixer and/or a sparging, via the monitoring unit with an open loop and/or closed loop control unit, when the capacitive sensor unit arranged at the first situation position or the second situation position or the third situation position is triggered.

11. The method according to claim 10 comprising monitoring, open-loop control and/or closed-loop control of foam formation in the bioreactor plant using the monitoring unit based on the transmitted data.

12. The method according to claim 10, wherein open-loop control and/or closed-loop control comprises feeding a substance that is designed to prevent or at least reduce foam formation when the presence of foam is detected by at least one capacitive sensor unit, preferably when the presence of foam is detected by at least one capacitive sensor unit at a situating position outside of the single-use container, in particular using a capacitive arc sensor unit.

13. The method according to claim 10, comprising:

Trigger an alarm when the presence of foam is detected by at least one capacitive sensor unit at a situating position in the interior of the single-use container and/or Trigger an alarm and/or an emergency shutoff when the presence of foam is detected by at least one capacitive sensor unit at a situating position outside of the single-use container.

* * * * *